US009867854B2

(12) United States Patent
Oh et al.

(10) Patent No.: US 9,867,854 B2
(45) Date of Patent: Jan. 16, 2018

(54) THERAPEUTIC METHOD USING CARDIAC TISSUE-DERIVED PLURIPOTENT STEM CELLS

(71) Applicant: Kyoto University, Kyoto (JP)

(72) Inventors: Hidemasa Oh, Kyoto (JP); Kento Tateishi, Kyoto (JP); Hiroaki Matsubara, Kyoto (JP)

(73) Assignee: Kyoto University, Kyoto (JP)

( * ) Notice: Subject to any disclaimer, the term of this patent is extended or adjusted under 35 U.S.C. 154(b) by 99 days.

(21) Appl. No.: 14/926,583

(22) Filed: Oct. 29, 2015

(65) Prior Publication Data

US 2016/0228472 A1 Aug. 11, 2016

Related U.S. Application Data

(62) Division of application No. 11/885,111, filed as application No. PCT/JP2006/304111 on Mar. 3, 2006, now abandoned.

(30) Foreign Application Priority Data

Mar. 4, 2005 (JP) ................................ 2005-060831

(51) Int. Cl.
| | |
|---|---|
| *C12N 5/00* | (2006.01) |
| *A61K 35/34* | (2015.01) |
| *A61L 27/38* | (2006.01) |
| *C12N 5/074* | (2010.01) |
| *C12N 5/077* | (2010.01) |
| *C12N 5/0775* | (2010.01) |
| *C12N 5/071* | (2010.01) |
| *A61K 35/12* | (2015.01) |

(52) U.S. Cl.
CPC .......... *A61K 35/34* (2013.01); *A61L 27/3873* (2013.01); *A61L 27/3895* (2013.01); *C12N 5/0607* (2013.01); *C12N 5/0661* (2013.01); *C12N 5/0662* (2013.01); *C12N 5/0668* (2013.01); *C12N 5/0691* (2013.01); *A61K 35/12* (2013.01); *A61L 2430/20* (2013.01); *C12N 2501/11* (2013.01); *C12N 2501/115* (2013.01); *C12N 2501/70* (2013.01); *C12N 2506/03* (2013.01); *C12N 2506/1315* (2013.01)

(58) Field of Classification Search
None
See application file for complete search history.

(56) References Cited

U.S. PATENT DOCUMENTS

| 7,862,810 | B2 | 1/2011 | Anversa |
| 2003/0082153 | A1 | 5/2003 | Epstein et al. |
| 2005/0058633 | A1 | 3/2005 | Epstein et al. |
| 2005/0079606 | A1 | 4/2005 | Tamaki et al. |
| 2007/0212423 | A1 | 9/2007 | Epstein et al. |

FOREIGN PATENT DOCUMENTS

| EP | 1437406 A2 | 7/2004 |
| WO | 2003027281 A2 | 4/2003 |
| WO | 2003035838 A2 | 5/2003 |
| WO | 2004019767 A2 | 3/2004 |
| WO | 2005003334 A2 | 1/2005 |

OTHER PUBLICATIONS

International Preliminary Report on Patentability and English translation issued in PCT/JP2006/304111, dated Dec. 5, 2006, pp. 1-13 in PDF.
Office Action issued in U.S. Appl. No. 11/885,111, dated Oct. 11, 2011, pp. 1-6 in PDF.
Submission of Claims from Counterpart JP patent Grant and Allowed Claims in Counterpart EPO Application as filed in U.S. Appl. No. 11/885,111, dated Nov. 10, 2011, pp. 1-30 in PDF.
Office Action issued in U.S. Appl. No. 11/885,111, dated Dec. 30, 2011, pp. 1-6 in PDF.
Office Action issued in U.S. Appl. No. 11/885,111, dated Nov. 8, 2012, pp. 1-5 in PDF.
Office Action issued in U.S. Appl. No. 11/885,111, dated Apr. 24, 2013, pp. 1-5 in PDF.
Office Action issued in U.S. Appl. No. 11/885,111, dated Sep. 26, 2013, pp. 1-2 in PDF.
Office Action issued in U.S. Appl. No. 11/885,111 dated Oct. 7, 2014, pp. 1-6 in PDF.
Office Action issued in U.S. Appl. No. 11/885,111, dated Jul. 30, 2015, pp. 1-7 in PDF.
Proksch, S. et al., "Does the Human Skeletal Muscle Harbor the Murine Equivalents of Cardiac Precursor Cells?," Molecular Therapy, vol. 17, No. 4, pp. 733-741, Apr. 2009.
Winitsky, S.O. et al., "Adult Murine Skeletal Muscle Contains Cells That Can Differentiate into Beating Cardiomyocytes in Vitro," PLoS Biology, vol. 3, No. 4, e87, pp. 662-671, Apr. 2005.
"Molecular Therapy," American Society of Gene & Cell Therapy, 2013, available at: http://www.nature.com/mt/index.html, last accessed Jul. 2, 2013, pp. 1-3.
Guan, K. et al., "Do stem cells in the heart truly differentiate into cardiomyocytes?," Journal of Molecular and Cellular Cardiology, vol. 43, pp. 377-387, Jul. 2007.
Office action for U.S. Appl. No. 10/863,004, dated May 18, 2006, pp. coverpage, 1-15.
Office action for U.S. Appl. No. 11/747,060, dated Dec. 15, 2009, pp. coverpage, 1-10.
Office action for U.S. Appl. No. 10/003,400, dated Feb. 5, 2004, pp. coverpage, 1-9.
Amendment and Response to Non-Final Office action for U.S. Appl. No. 10/863,004, dated Oct. 18, 2006, pp. 1-9.
Amendment and Response to Non-Final Office action for U.S. Appl. No. 11/747,060, dated May 14, 2010, pp. 1-8.
Notice of Abandonment for U.S. Appl. No. 10/003,400, dated Oct. 5, 2004, pp. coverpage and 1.

(Continued)

*Primary Examiner* — Blaine Lankford
(74) *Attorney, Agent, or Firm* — Pearne & Gordon LLP

(57) ABSTRACT

An object of the present invention is to provide a stem cell applicable to regenerative therapeutic method, and to provide a technique to carry out regenerative therapy using the cell. A collected cardiac tissue fragment is enzymatically treated to prepare a cell suspension. Then using the cell suspension, following steps are carried out: (1) separation of cells by the density gradient method, (2) suspension-culture in a culture medium containing fibroblast growth factor and epidermal growth factor and (3) selection and separation of cells forming a floating sphere to obtain pluripotent stem cells. Thus-obtained pluripotent stem cells are used to carry out regenerative therapy.

18 Claims, 13 Drawing Sheets

(56) References Cited

OTHER PUBLICATIONS

"*Homo sapiens* (ID 51)—Genome—NCBI," National Center for Biotechnology Information, 2013, available at: http://www.ncbi.nlm.nih.gov/genome/51, last accessed Jul. 3, 2013, pp. 1-2.
"Mus musculus (ID 52)—Genome—NCBI," National Center for Biotechnology Information, 2013, available at: http://http://www.ncbi.nlm.nih.gov/genome?term=mus%20musculus, last accessed Jul. 3, 2013, pp. 1-3.
European Office action for European Application No. 10 179 375.0, dated Oct. 2, 2013, pp. registered letter 1-2 and form 2906 1-2.
Tsai, M.S. et al., "Isolation of human multipotent mesenchymal stem cells from second-trimester amniotic fluid using a novel two-stage culture protocol," Human Reproduction, vol. 19, No. 6, pp. 1450-1456, Apr. 2004.
Takehara Declaration Under 37 CFR 1.132, dated Oct. 22, 2013, filed in U.S. Appl. No. 11/885,111 in response to the Advisory Action dated Sep. 26, 2013, and the Office action dated Apr. 24, 2013.
Wehman, B. et al., "The Emergence of Stem Cell Therapy for Patients with Congenital Heart Disease," Circulation Research, 116:566-569 (2015) and cover page.
Ishigami, S. et al., "Intracoronary Autologous Cardiac Progenitor Cell Transfer in Patients with Hypoplastic Left Heart Syndrome: The TICAP Prospective Phase I Controlled Trial," Circulation Research, 116:653-664 (2015), supplemental pp. 1-16, and cover page.
Dubois, N.C. et al., "SIRPA is a specific cell-surface marker for isolating cardiomyocytes derived from human pluripotent stem cells," Nature Biotechnology, 29:1011-1018 (2011) and Online Methods page.
Tateishi, K. et al., "Human cardiac stem cells exhibit mesenchymal features and are maintained through Akt/GSK-3b signaling," Biochemical and Biophysical Research Communications, 352:635-641 (2007).
Declaration Under 37 CFR 1.132 of Hidemasa Oh, dated Apr. 6, 2015, filed in U.S. Appl. No. 11/885,111 in response to the Office action dated Oct. 7, 2014.
Oh et al., Cardiac progenitor cells from adult myocardium: Homing, differentiation, and fusion after infarction; PNAS, Oct. 14, 2003, vol. 100, No. 21, pp. 12313-12318.
Hierlihy, et al., The post-natal heart contains a myocardial stem cell population; FEBS Letters, 2002, vol. 530, pp. 239-243.
Messina, et al., Isolation and Expansion of Adult Cardiac Stem Cells from Human and Murine Heart; Circulation Research, 2004, vol. 95: 911-921.
Messina, et al., Isolation and Expansion of Adult Cardiac Stem Cells from Human and Murine Heart; Circulation Research, 2004, vol. 95, Supplemental material, pp. 1-23 in PDF.
Beltrami et al., Adult Cardiac Stem Cells Are Multipotent and Support Myocardial Regeneration, Cell, Sep. 19, 2003, vol. 114, pp. 763-776.
Communication issued in the Supplementary European Search Report for European Patent Application No. 06715194.4-PCT/JP2006304111; dated Jul. 16, 2008, pp. 1-7 in PDF.
Office Action dated Sep. 14, 2010 issued in Japanese Patent Application No. 2007-506027.
Tateishi et al., Clonal Isolation and Characterization of Multipotent Adult Progenitor Cells from Mammalian Heart: Therapeutic Potential for Severe Heart Failure, Journal Cardiac Failure, vol. 11, No. 9, p. S71, Abstract YIA-003, Dec. 1, 2005.
European Office action for European Patent Application No. 10 179 375.0, dated Jan. 28, 2011, pp. 1-6 in PDF.
Tarui et al., "Transcoronary infusion of cardiac progenitor cells in hypoplastic left heart syndrome . . . ," J. Thorac. Cardiovasc. Surg. 2015, vol. 150, pp. 1198-1208, submitted in "Article in Press" format, pp. 1-14 of pdf (published as 2015, vol. 150, pp. 1198-1207).
Ishigami et al., "Intracoronary Cardiac Progenitor Cells in Single Ventricle Physiology . . . ," Circ. Res. 2017, vol. 120, pp. 1162-1173.
Takehara, et al., "Controlled Delivery of Basic Fibroblast Growth Factor Promotes Human Cardiosphere-Derived Cell Engraftment to Enhance Cardiac Repair for Chronic Myocardial Infraction", Journal of the American College of Cardiology, vol. 52, No. 23, pp. 1858-1865, Dec. 2, 2008.
Shamblott, et al., "Derivation of pluripotent stem cells from cultured human primordial germ cells", Proceedings of the National Academy of Sciences, USA, vol. 95, pp. 13726-13731, 1998.
Casselli, et al., "Human atria are a feasible source of multipotent adult progenitor cells", European Heart Journal, vol. 26, p. 222, Abstract 1460, Sep. 2005.
Beltrami, et al., "Multipotent cells can be generated in vitro from several adult human organs . . . " Blood, vol. 110, pp. 3438-3446, Nov. 1, 2007.
Cesselli, et al., "Multipotent Progenitor Cells Are Present in Human Peripheral Blood", Circulation Research, vol. 104, pp. 1225-1234, 2009.
Goumans, et al., "Human Cardiac Progenitor Cells are Able to Differentiate into Cardiomyocytes in Vitro", Circulation (Supplement II), vol. 112, p. II-52, Abstract 337, Oct. 25, 2005.
Takamiya, et al., "Identification and Characterization of a Novel Multipotent Sub-Population of Sca-1+ Cardiac Progenitor Cells for Mycocardial Regeneration", PLoS ONE, vol. 6, pp. 1-11, 2011.
Yamahara, et al., "Heterogeneic nature of adult cardiac side population cells", Biochemical and Biophysical Research Communications, vol. 371, pp. 615-620, Apr. 14, 2008.
Pfister, et al., "CD31- but Not CD31+ Cardiac Side Population Cells Exhibit Functional Cardiomyogenic Differentiation", Circulation Research, vol. 97, pp. 52-61, 2005.
Martin, et al., "Persistent expression of the ATP-binding cassette transporter, Abcg2, identifies cardiac SP cells in the developing and adult heart", Developmental Biology, vol. 265, pp. 262-275, 2004.
Howell, et al., "Pluripotent Stem Cells Identified in Multiple Murine Tissues", Ann. N.Y. Acad. Sci., vol. 996, pp. 158-173, 2003.
Tateishi, et al., "Clonally amplified cardiac stem cells are regulated by Sca-1 signaling for efficient cardiovascular regeneration", Journal of Cell Science, vol. 120, pp. 1791-1800, 2007.
Notice of Opposition issued in European Application No. 10179375.0, dated Feb. 3, 2017, pp. 1-24.

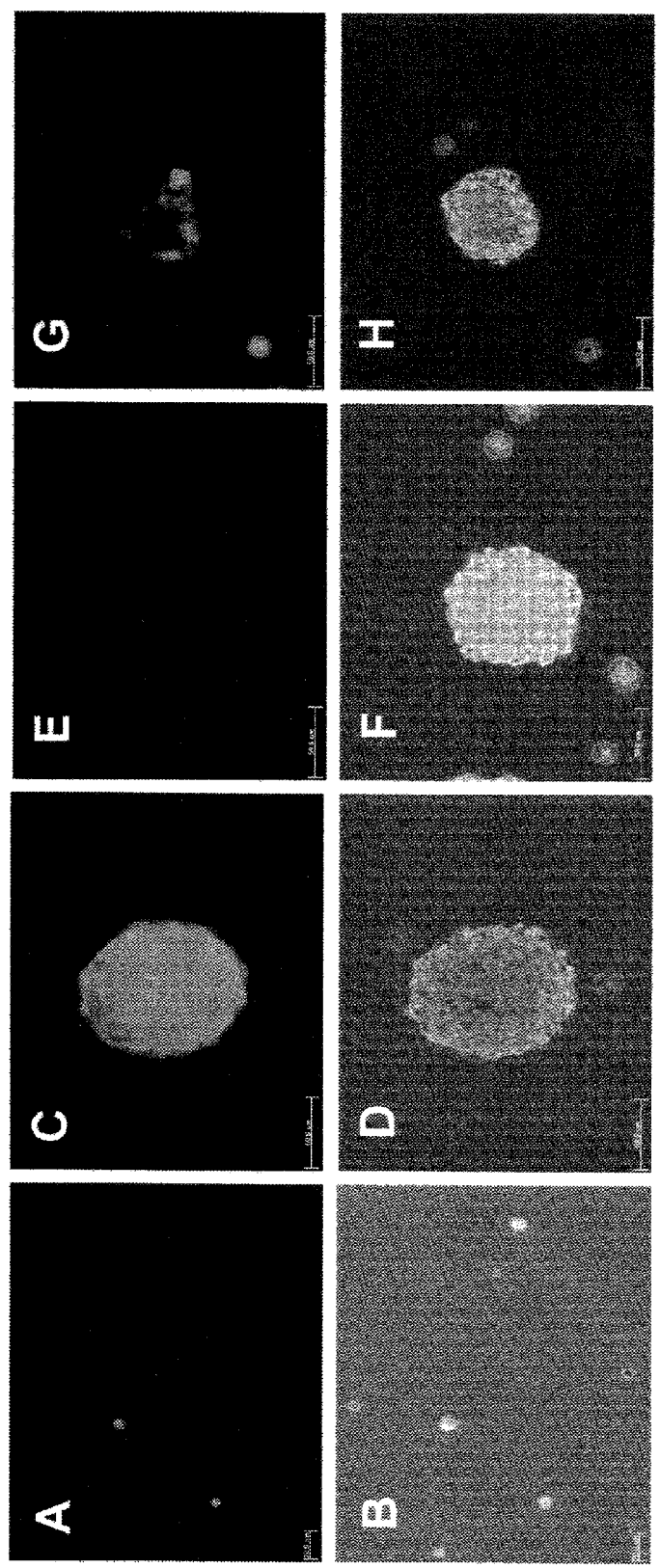
[Fig.1]

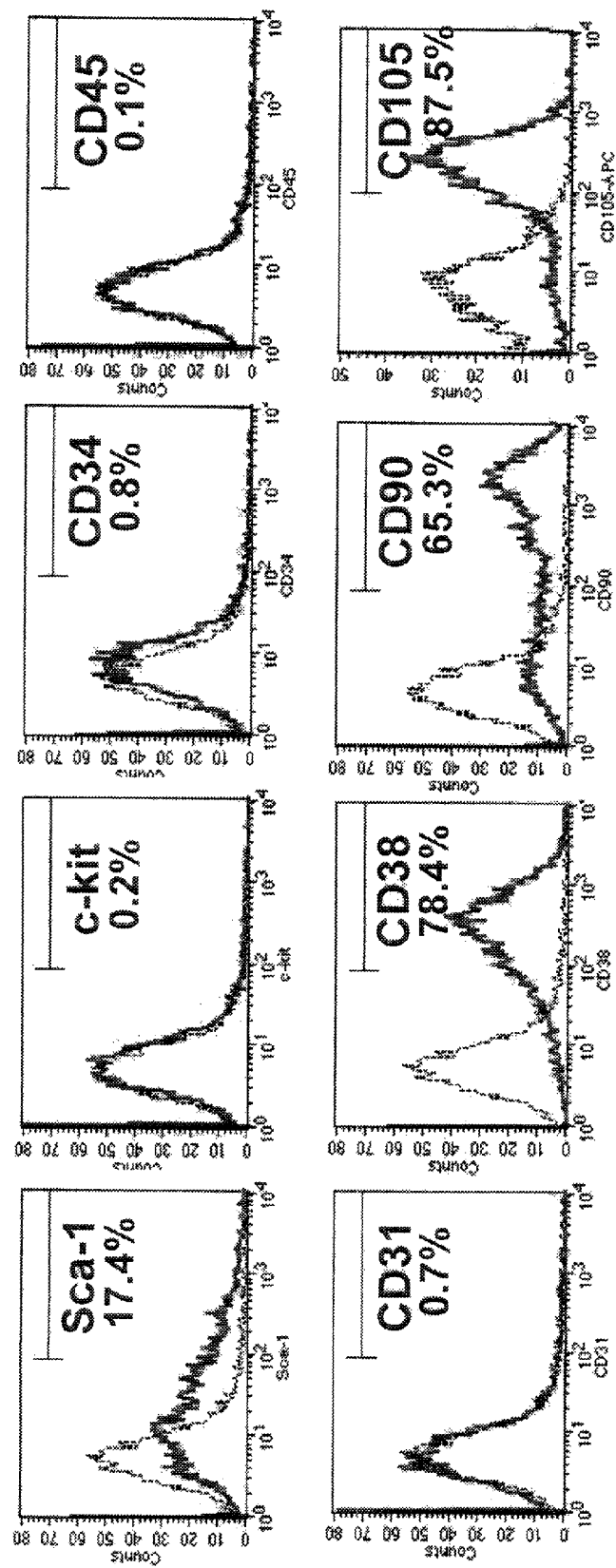
[Fig.2]

[Fig.3]
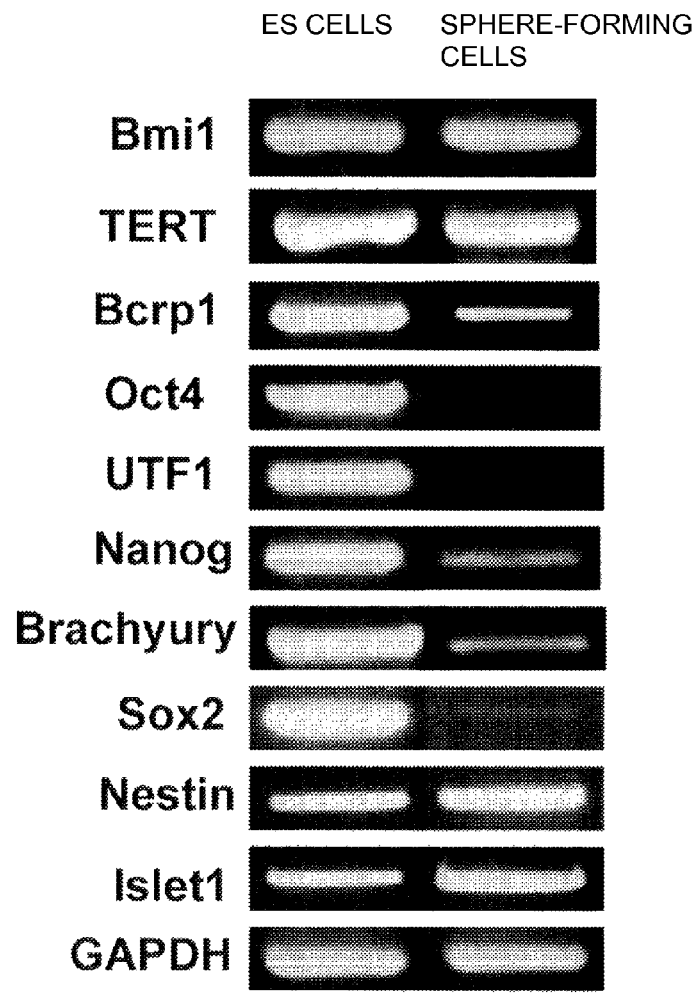
[Fig.4]
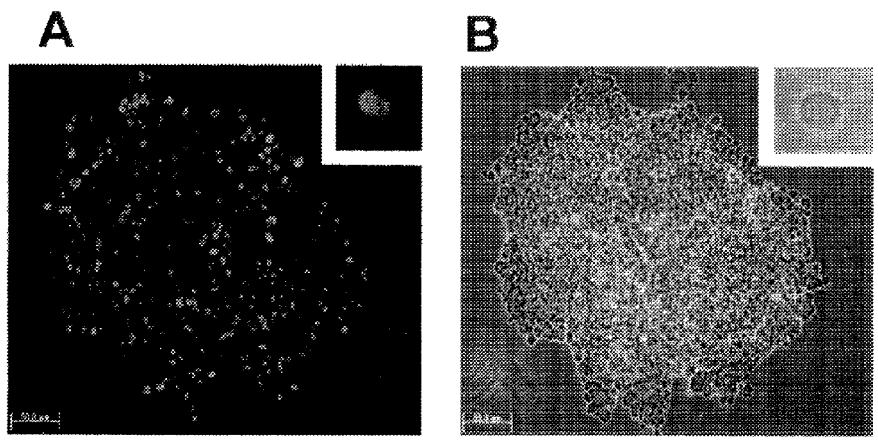

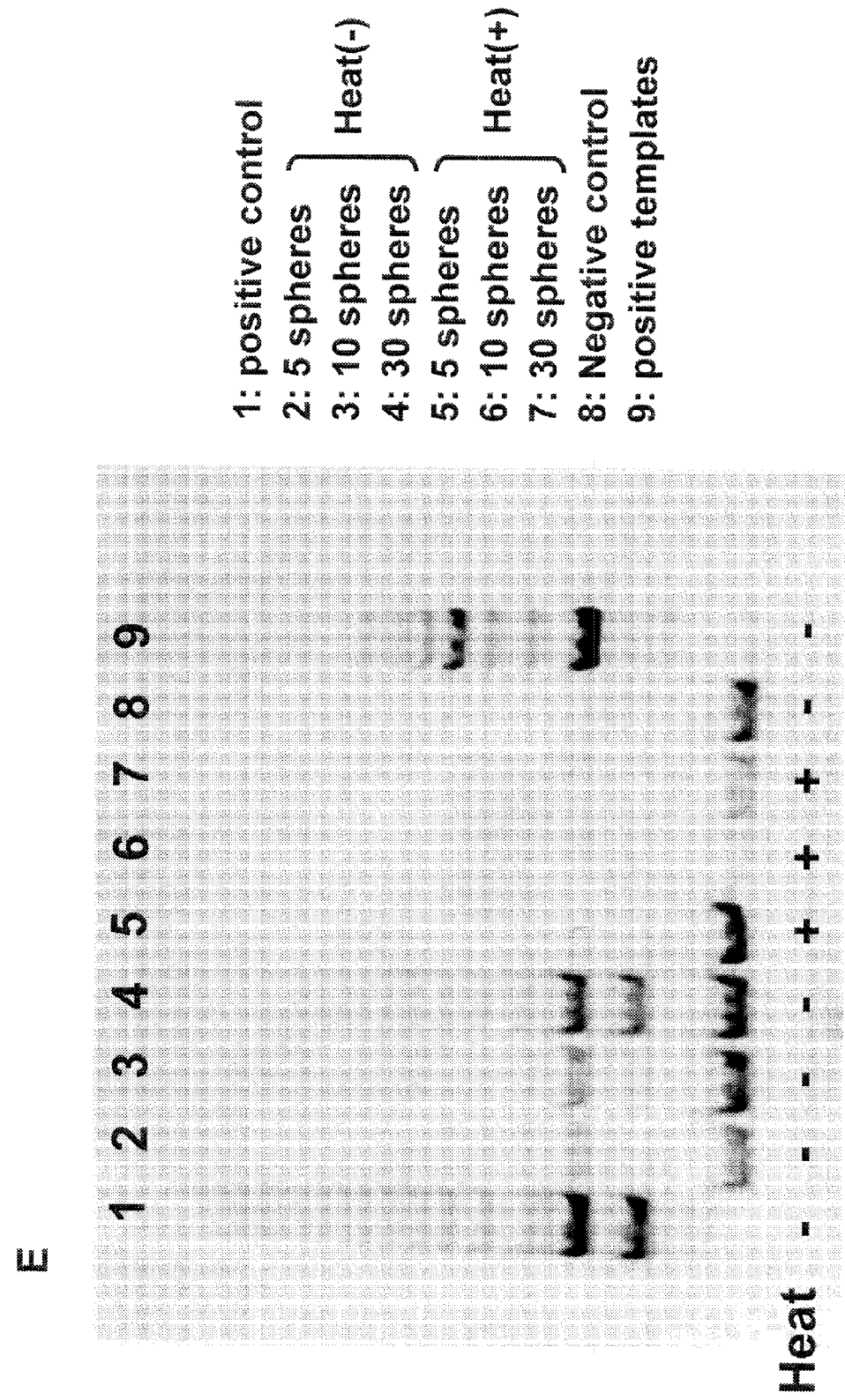

[Fig.6]
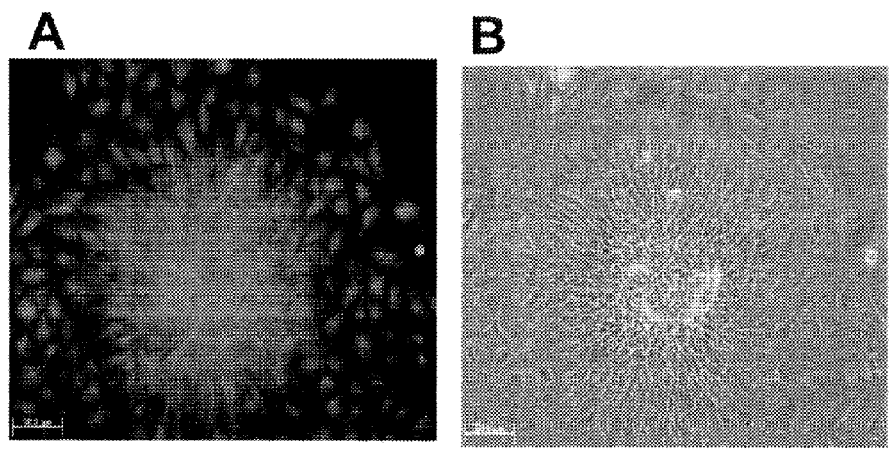
[Fig.7]
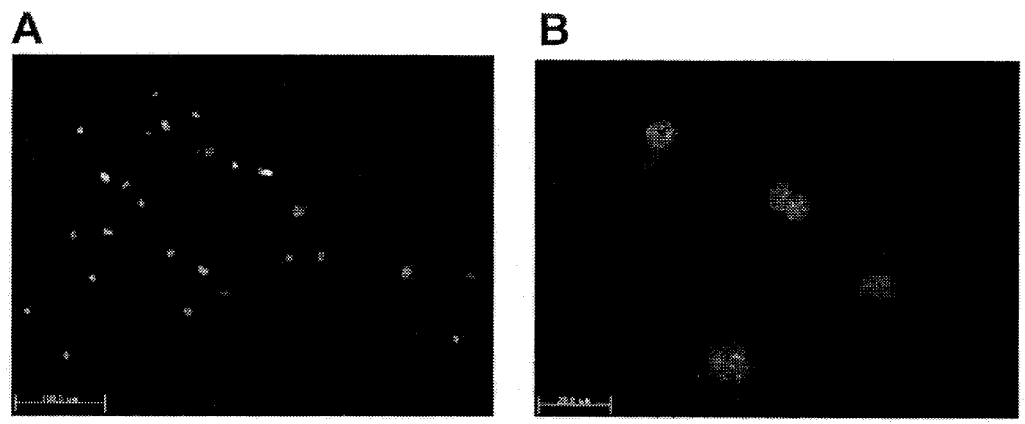

[Fig.8]
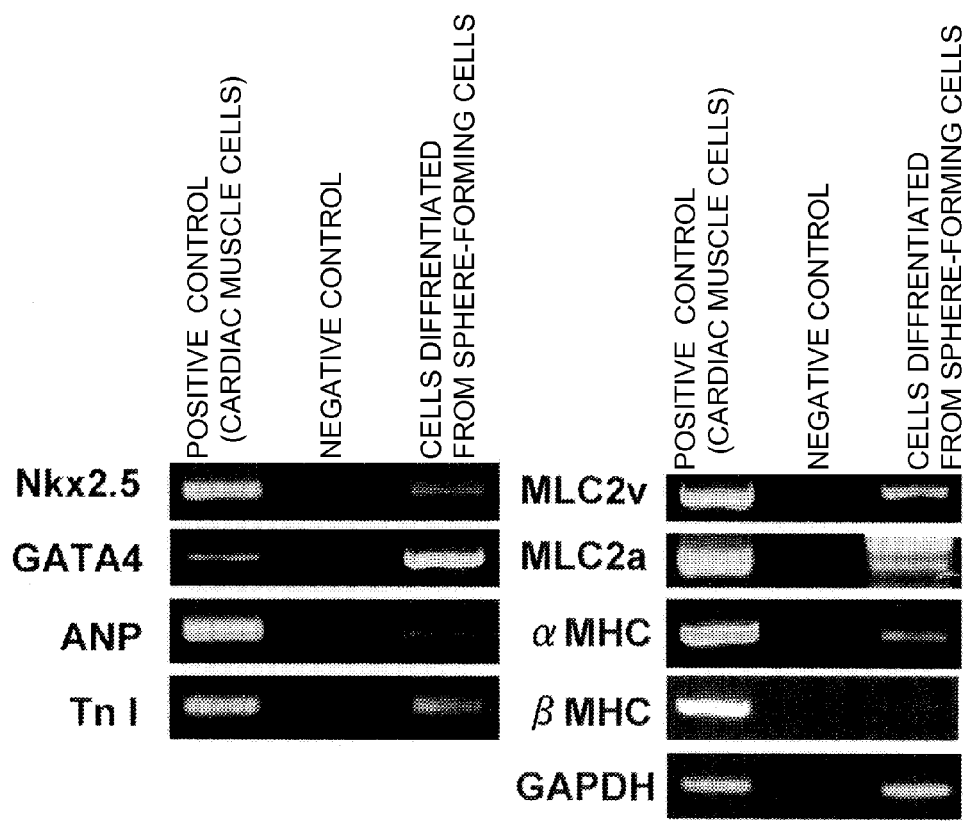

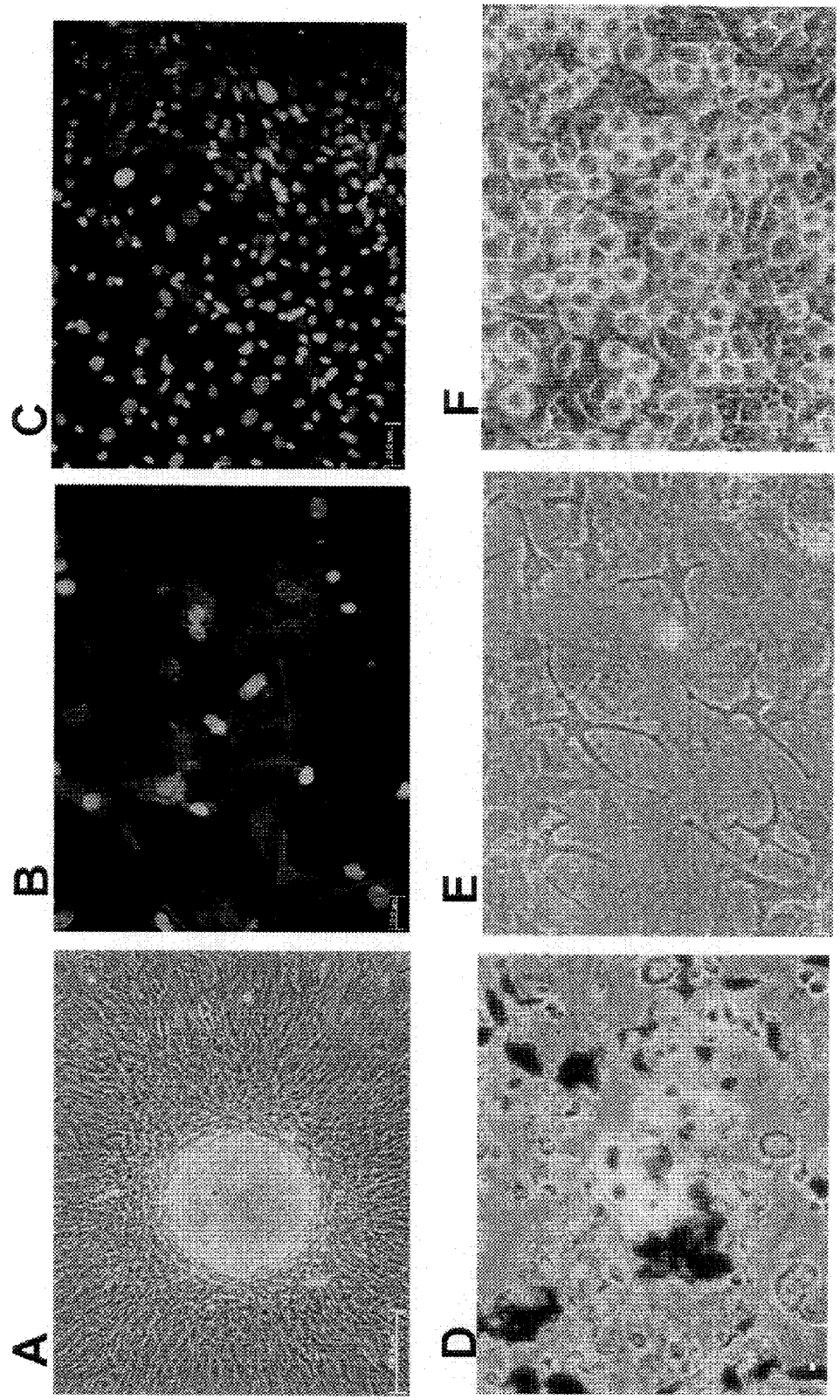
[Fig.9]

[Fig.10]
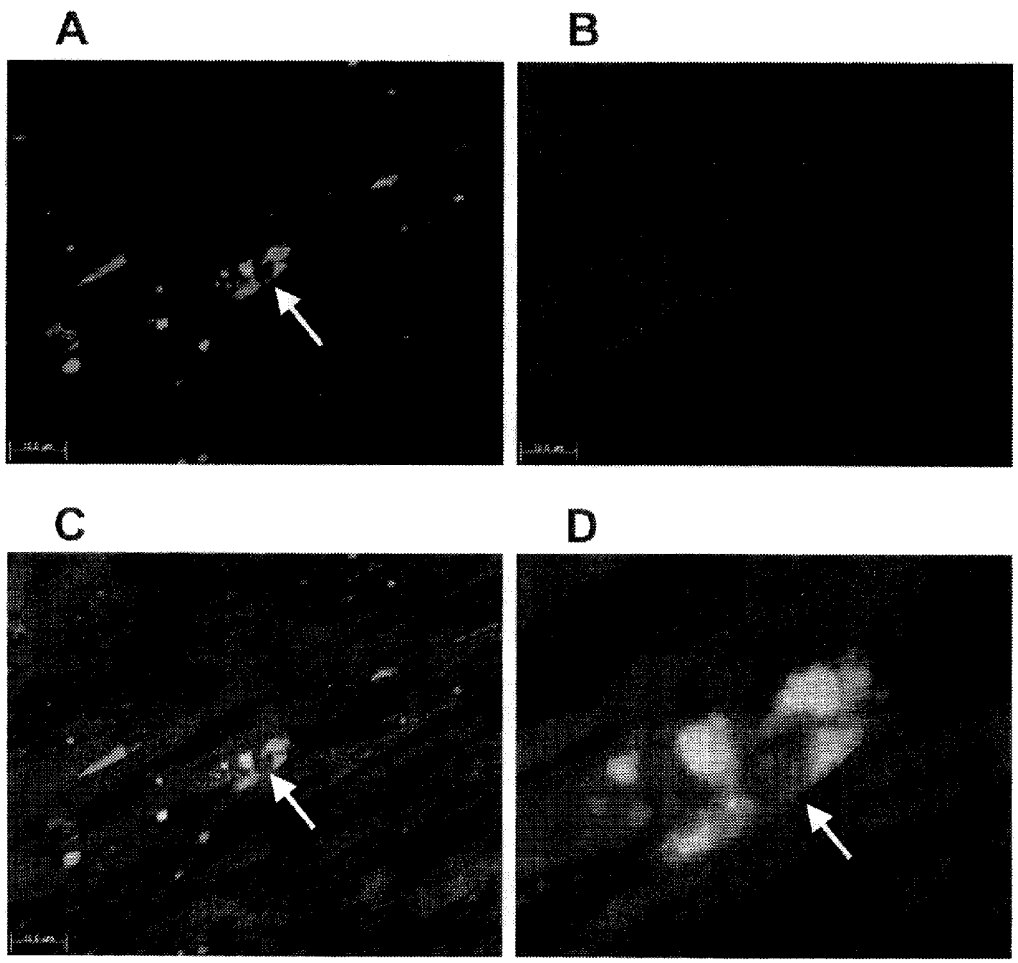
[Fig.11]
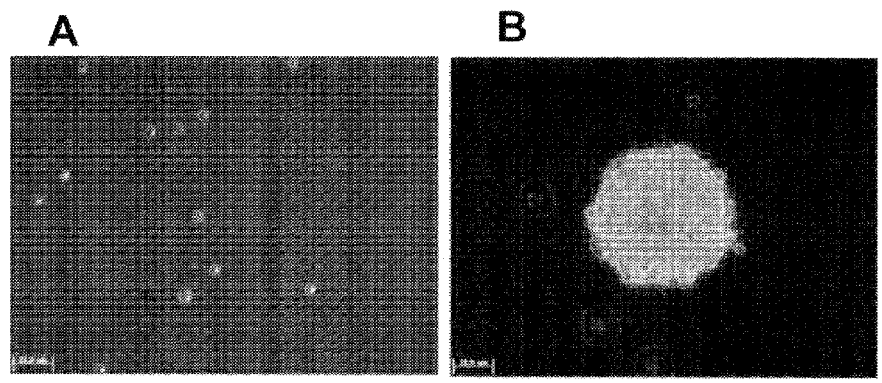

[Fig.12]
[Fig.13]
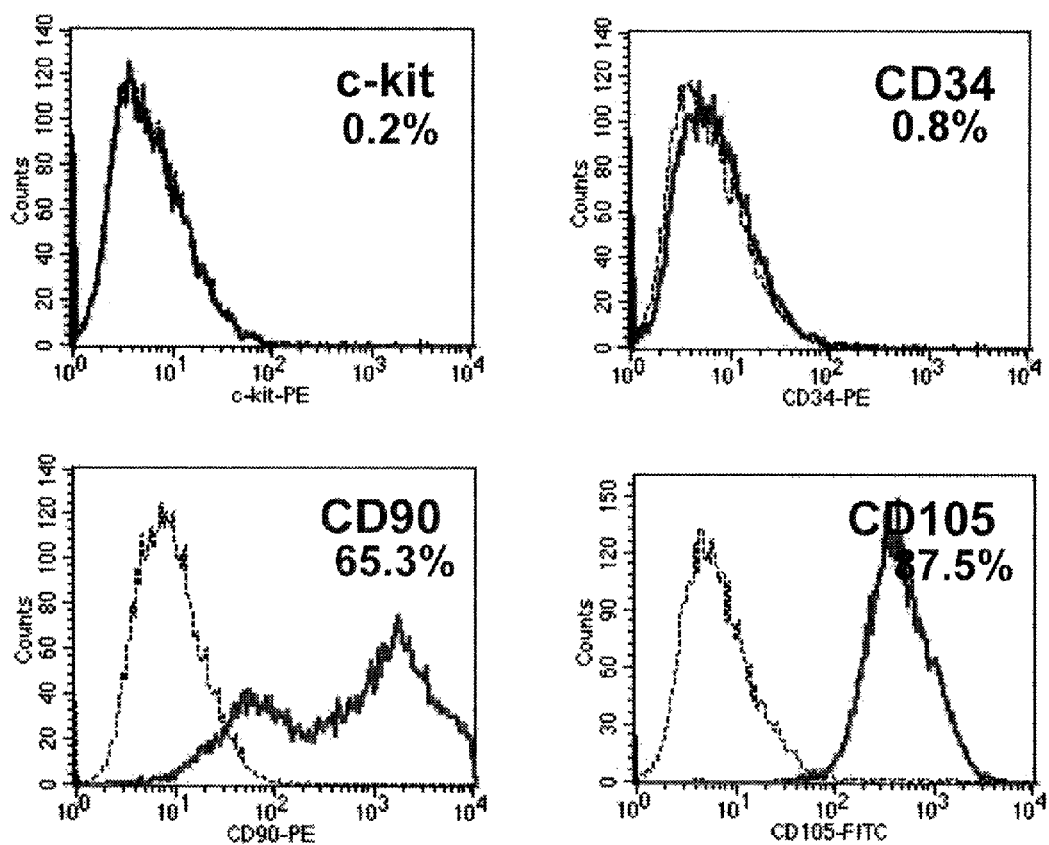

[Fig.14]
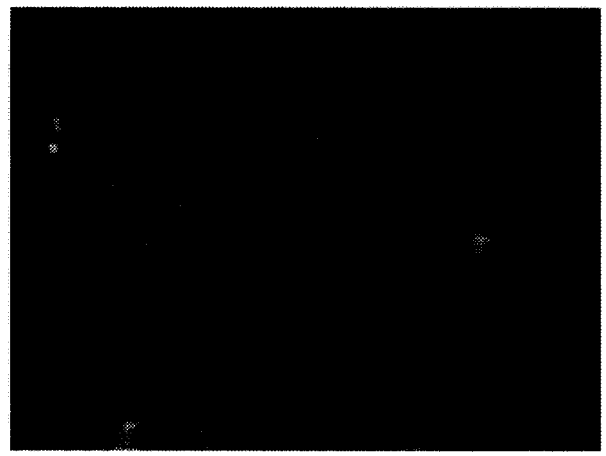
[Fig.15]
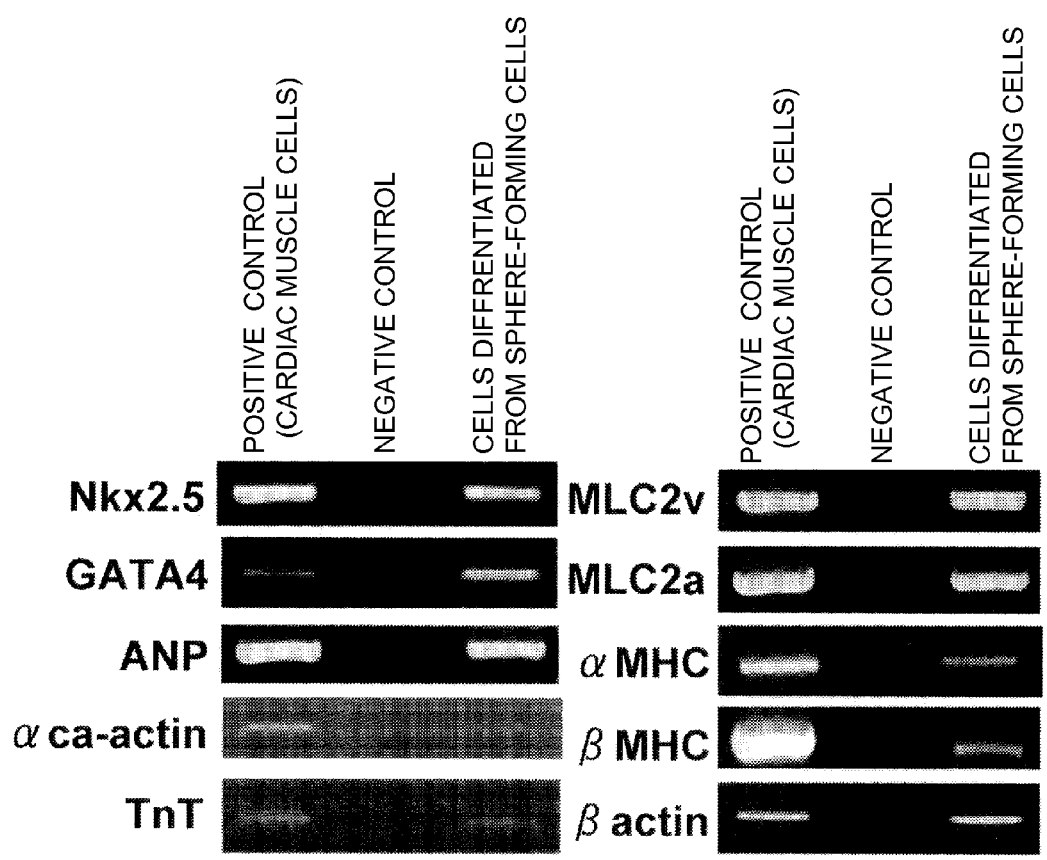

[Fig.16]
[Fig.17]
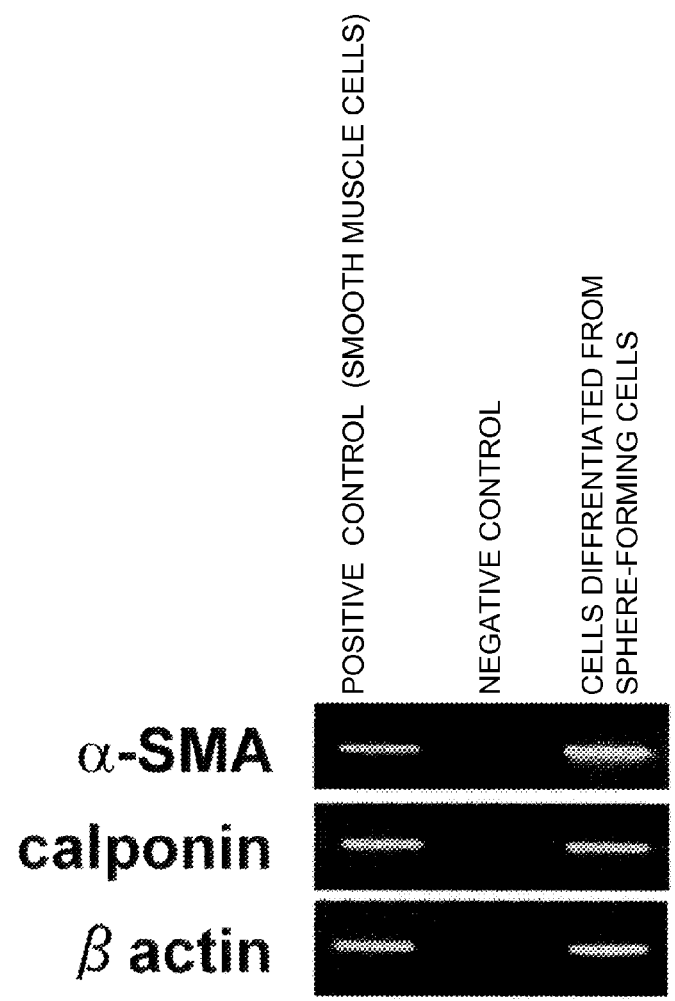

[Fig.18]
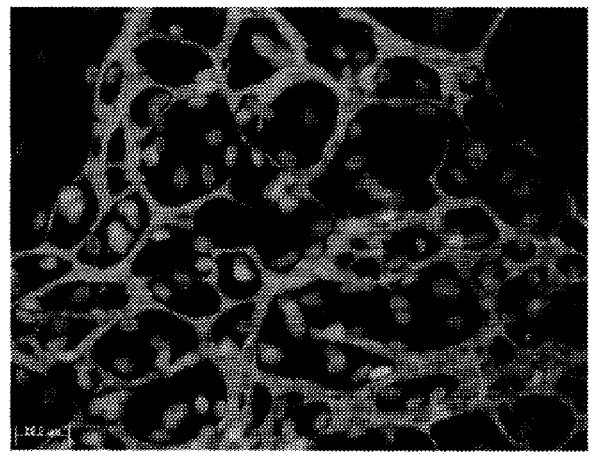
[Fig.19]
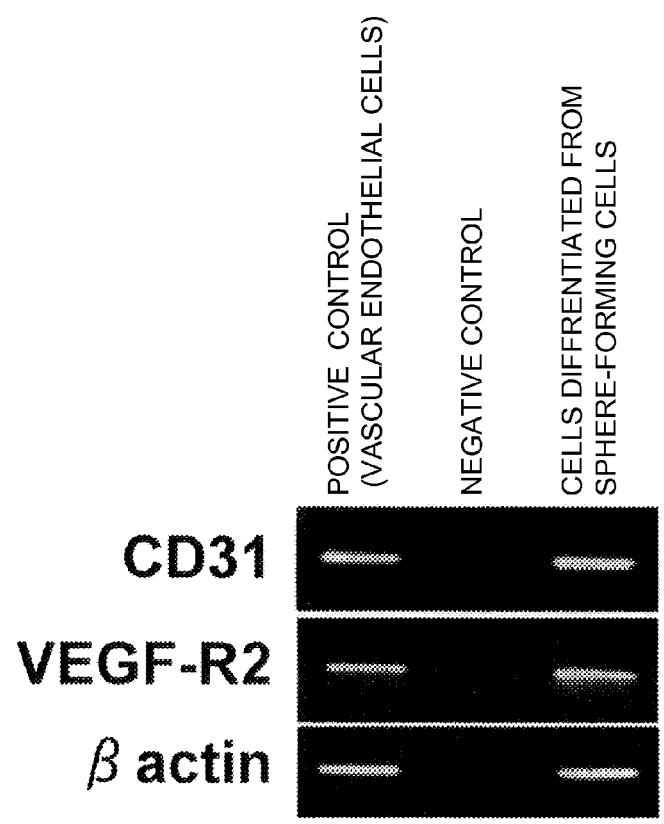

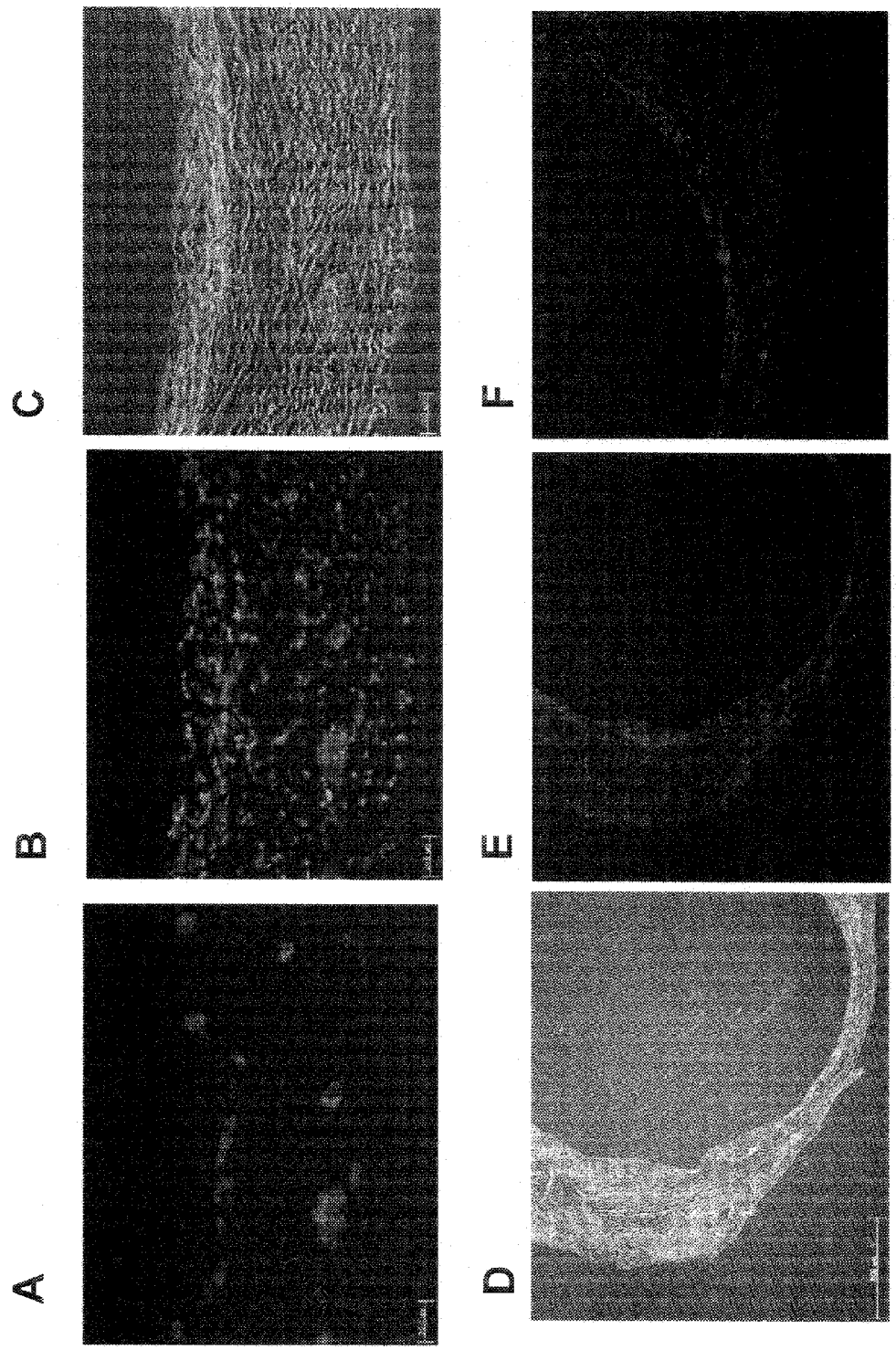
[Fig.20]

THERAPEUTIC METHOD USING CARDIAC TISSUE-DERIVED PLURIPOTENT STEM CELLS

CROSS-REFERENCE TO RELATED APPLICATIONS

This application is a divisional of application Ser. No. 11/885,111, filed Jun. 3, 2008, which is a national stage application of International Application PCT/JP2006/304111, filed Mar. 3, 2006, and which claims priority of Japanese application No. 2005-060831, filed Mar. 4, 2005, all of which are hereby incorporated by reference.

TECHNICAL FIELD

The present invention relates to a cardiac tissue-derived pluripotent stem cell, and in particular to a pluripotent stem cell having excellent differentiation capability into cardiac myocyte. Furthermore, the present invention relates to a preparation method for the stem cell, and to a therapeutic method for cardiac disease using the stem cell.

BACKGROUND ART

In recent years, medical technologies have been actively studied in the field of regenerative medicine, whereby a stem cell is transplanted to repair and regenerate target tissue and organ. Thus far, stem cells differentiating into mature cells of various tissues and organs have been discovered, clinical application in cell transplantation has been investigated.

For instance, c-kit-negative/CD31-positive/CD34-negative/Sca-1-positive mouse stem cell (refer to Oh H., et. Al., "Cardiac progenitor cells from adult myocardium: Homing, differentiation, and fusion after infarction", Proc Natl Acad Sci USA, Vol. 100, 12313-12318, Oct. 14, 2003) and c-kit-positive/CD31-positive/CD34-positive rat stem cell (refer to Messina E., et. Al., "Isolation and expansion of adult cardiac stem cells from human and murine heart", Circ Res., Vol. 95, 911-921, 2004 and Beltrami A P., et. Al., "Adult cardiac stem cells are multipotent and support myocardial regeneration", Cell, Vol. 114, 763-776, Sep. 19, 2003) have been reported as cardiac tissue-derived myocardial stem cells. However, no studies have been carried out in human with the former myocardial stem cell, leaving clinical applicability unclear. Also, with the latter myocardial stem cell, proliferative ability is poor in addition to the isolation being extremely difficult, and there is the disadvantage that it is not suitable for large-scale culture for transplantation purposes. In addition, both above-mentioned myocardial stem cells are not pluripotent stem cells, and applications thereof are only to cell transplantation in heart.

In addition, in regard to myocardial stem cells, search for stem cells differentiating into cardiac myocyte is under way around bone marrow-derived hematopoietic cells and mesenchymal stem cells, in addition to cardiac tissue-derived myocardial stem cells; however, cells reported in prior art are not clinically applicable as the degree of differentiation into cardiac myocyte is extremely low.

As stated above, although cells that may function as stem cells have been found, the current situation is that almost none that are actually clinically applicable are known. With such prior art as the background, development is desired, of a pluripotent stem cell capable of differentiating into various mature cells such as cardiac myocyte, and applicable to regenerative therapeutic method.

Note that, so far, c-kit-negative/c-met-negative/CD34-negative/Sca-1-negative/Pax (3/7)-negative cardiac myocyte progenitor cells of muscle origin have been reported to be capable of differentiating into spontaneously beating cardiac myocyte (refer to WO2003/035838). However, the stem cell described in this WO2003/035838 can be isolated taking the muscle as the origin, and is known to be non-isolable from cardiac tissue (refer to Example 11 in WO2003/035838).

DISCLOSURE OF THE INVENTION

Problems to be Solved by the Invention

It is an object of the present invention to resolve the above-mentioned problems of the prior art. In detail, it is an object of the present invention to provide a stem cell applicable to regenerative therapeutic method, and to provide a technique to carry out regenerative therapy using the cell.

Means for Solving the Problems

The present inventors conducted earnest studies to solve the above problems, and found that a pluripotent stem cell in particular with excellent differentiation capability into cardiac myocyte could be obtained by treating enzymatically a collected cardiac tissue fragment to prepare a cell suspension, and use the cell suspension to perform (1) cell separation by a density gradient method, (2) suspension culture in a culture medium containing fibroblast growth factor and epidermal growth factor, and (3) selection and separation of cell mass forming a floating sphere. In addition, the stem cell is excellent not only in the above-mentioned differentiation capability but also from the point of self-renewal capability, confirming applicability in regenerative therapy by cell transplantation. The present invention was completed by further studies based on these observations.

That is to say, the present invention provides the preparation methods for pluripotent stem cell mentioned in the following:

Item 1. A method for preparing a mammalian cardiac tissue-derived pluripotent stem cell prepared by the steps of:
 (i) enzymatically treating a cardiac tissue fragment collected from a mammal to prepare a cell suspension;
 (ii) separating a group of cardiac tissue-derived cells from the above cell suspension by the density gradient method; and
 (iii) suspension-culturing the obtained group of cardiac tissue-derived cells in a culture medium containing fibroblast growth factor and epidermal growth factor, and then selecting and separating cells forming a floating sphere.

Item 2. The method according to Item 1, in which the pluripotent stem cells are c-kit-negative, CD31-negative and CD34-negative.

Item 3. The method according to Item 2, in which the pluripotent stem cells are further CD105-positive.

Item 4. The method according to Item 1, in which the pluripotent stem cells are human-derived.

Item 5. The method according to Item 1, in which the pluripotent stem cells have the capability to differentiate at least into a cardiac myocyte.

Item 6. The method according to Item 1, in which the pluripotent stem cells have the capability of differentiating into one or more species of cells selected from the group consisting of cardiac myocyte, smooth myocyte, vascular endothelial cell, adipocyte, glial cell and epithelial cell.

In addition, the present invention provides the pluripotent stem cells mentioned in the following:

Item 7. Mammalian cardiac tissue-derived pluripotent stem cell obtained by the method according to any one of Items 1 to 6.

Item 8. A mammalian cardiac tissue-derived pluripotent stem cell, which is c-kit-negative, CD31-negative and CD34-negative.

Item 9. The stem cell according to Item 8, which is CD105-positive.

Item 10. The stem cell according to Item 8, in which the mammal is a human.

Item 11. The stem cell according to Item 8, which is a pluripotent stem cell having the capability of differentiating at least into a cardiac myocyte.

Item 12. The stem cell according to Item 8, which is a pluripotent stem cell having the capability of differentiating into one or more species of cells selected from the group consisting of cardiac myocyte, smooth myocyte, vascular endothelial cell, adipocyte, glial cell and epithelial cell.

In addition, the present invention provides the therapeutic methods mentioned in the following:

Item 13. A therapeutic method for an organ or a tissue disease, wherein a therapeutically effective amount of the stem cells according to any one of Items 8 to 12 is transplanted into a tissue or an organ of a patient.

Item 14. The therapeutic method according to Item 13, which is a therapeutic method for cardiac disease.

Item 15. The therapeutic method according to Item 13, which is a therapeutic method for cardiac disease, comprising the following steps of:
(i) enzymatically treating a cardiac tissue fragment collected from a human to prepare a cell suspension;
(ii) separating a group of cardiac tissue-derived cells from said cell suspension by a density gradient method;
(iii) suspension-culturing the obtained group of cardiac tissue-derived cells in a culture medium containing fibroblast growth factor and epidermal growth factor, and then selecting and separating cells forming a floating sphere;
(iv) proliferating the cells separated in the above Step (iii), and
(v) transplanting a therapeutically effective amount of the cells proliferated in the above Step (iv) into the heart of a cardiac disease patient.

Furthermore, the present invention provides the compositions mentioned in the following:

Item 16. A composition for the treatment of a tissue or organ disease, the composition comprising the stem cells according to any one of Items 8 to 12 and a pharmaceutically acceptable carrier.

Item 17. A composition for the treatment of cardiac disease, the composition comprising the stem cells according to any one of Items 8 to 12 and a pharmaceutically acceptable carrier.

And furthermore, the present invention provides the use of a stem cell in the modes mentioned in the following:

Item 18. Use of the stem cells according to any one of Items 8 to 12, for preparing a composition for the treatment of cardiac disease.

Item 19. Use of the stem cell according to any one of Items 8 to 12, for preparing a composition for the treatment of a tissue or organ disease.

Effects of the Invention

The present invention provides a stem cell derived from cardiac tissue, capable of differentiating into cardiac myocyte, vascular smooth myocyte, vascular endothelial cell or the like, and regenerating various tissues and organs such as heart. Thus, according to the pluripotent stem cell of the present invention, treatment of various tissue and organ diseases becomes possible, by a new methodology i.e. cell transplantation.

In addition, the pluripotent stem cell of the present invention has the advantage of being available by a simple method of suspension-culturing a group of cardiac tissue-derived cells under specific conditions to obtain a floating sphere, and is clinically highly useful. In addition, by obtaining a floating sphere in this way, stem cells grown from a single cell are selected and separated, giving also the advantage of high homogeneity of the stem cells per se, which is clinically highly useful.

Furthermore, the pluripotent stem cell of the present invention has excellent differentiation capability in particular into cardiac myocyte, allowing a patient of severe heart failure, who has no choice but to depend on heart transplantation, to be provided with a novel therapeutic method by cell transplantation, and is useful for a therapeutic method for cardiac disease that is an alternative to heart transplantation.

BRIEF DESCRIPTION OF THE DRAWINGS

FIG. 1 shows photographs of floating spheres (cell masses) formed after suspension culture of groups of mouse-derived cardiac tissue-derived cells separated by percoll density gradient centrifugation. A, C, E and G are photographs taken under a fluorescence microscope, B, D, F and H are photographs taken from a phase contrast microscope. A and B, C and D, E and F, G and H are the same visual fields photographed respectively. A and B show a state where wild-type mouse-derived sphere and GFP-expressing mouse-derived sphere are mixed and floating. C and D show a GFP-expressing mouse-derived sphere. E and F show a wild-type mouse-derived sphere. G and H show a sphere formed by mixed wild-type mouse-derived cells and GFP-expressing mouse-derived cells.

FIG. 2 shows results of FACS analysis of various cell surface antigens (Sca-1, c-kit, CD34, CD45, CD31, CD38, CD90 and CD105) of mouse-derived sphere-forming cells. In FIG. 2, thick (heavy) lines are analytical results for sphere-forming cells and thin (light) lines are analytical results for the controls (cells with no labeling).

FIG. 3 shows the results of analysis by PCR of the expression of various markers (Bmi 1, TERT, Bcrp 1, Oct 4, UTF 1, Nanog, Brachyury, Sox 2, Nestin, Islet 1) in mouse-derived sphere-forming cells and ES cells. Note that in the present analysis, GAPDH was used as control.

FIG. 4 shows the result of observation of bromodeoxyuridine (BrdU) expression for a floating sphere formed after suspension culture of a group of mouse-derived cardiac tissue-derived cells separated by percoll density gradient centrifugation. In FIG. 4, A shows an image of a BrdU-stained sphere, and B shows a phase contrast image of A.

FIG. 5 shows the result of analysis of telomerase expression for a floating sphere formed after suspension culture of a group of mouse-derived cardiac tissue-derived cells separated by percoll density gradient centrifugation.

FIG. 6 shows cell shapes observed in the process of inducing the differentiation of GFP-expressing mouse-derived sphere-forming cells into cardiac myocytes. In FIG. 6, A shows an image observed with fluorescence, and B shows the phase contrast image of the same visual field as A.

FIG. 7 shows photograph of cardiac myocytes differentiated from mouse-derived sphere-forming cells. In FIG. 7, B is a magnification of A.

FIG. 8 shows the result of analysis by PCR of the expression of various markers (Nkx 2.5, GATA 4, ANP, troponin-I (TnI), MLC2v, MLC2a, α-MHC (α-myosin heavy chain), β-MHC (β-myosin heavy chain), GAPDH) in a cardiac myocyte derived from a sphere-forming cell.

FIG. 9 shows photographs of sphere-forming cells, and various cells differentiated from said cells. In FIG. 9, A shows sphere-forming cells; B shows smooth myocytes differentiated from sphere-forming cells; C shows vascular endothelial cells differentiated from sphere-forming cells; D shows adipocytes differentiated from sphere-forming cells; E shows glial cells differentiated from sphere-forming cells; and F shows epithelial cells differentiated from sphere-forming cells.

FIG. 10 shows the state of grafting in a mouse cardiac muscle, wherein the mouse-derived sphere-forming cells (pluripotent stem cells) obtained in Example 1 were transplanted into an infarcted mouse cardiac muscle. A is a figure showing grafting of sphere-forming cells (green) in the host cardiac muscle. B is a figure showing the result of cTnT staining (presenting red color) in the same visual field as the above A. C is a figure overlaying the above A and B, and D is a figure magnifying the above C.

FIG. 11 shows photographs of floating spheres (cell masses) formed after suspension culture of groups of human-derived cardiac tissue-derived cells separated by percoll density gradient centrifugation. In FIG. 11, A shows spheres observed one day after culture, and B shows a sphere observed seven day after culture.

FIG. 12 shows the results of analysis by PCR of the expression of various markers (Rex 1, TERT, Oct 4, Nanog, Brachyury, Sox 2) in human-derived sphere-forming cells.

FIG. 13 shows the results of FACS analysis of various cell surface antigens (c-kit, CD34, CD90 and CD105) of human-derived sphere-forming cells. In FIG. 13, thick (heavy) lines are analytical results for sphere-forming cells and thin (light) lines are analytical results for the controls (cells with no labeling).

FIG. 14 shows photograph of cardiac myocytes differentiated from human-derived sphere-forming cells.

FIG. 15 shows the result of analysis by PCR of the expression of various markers (Nkx-2.5, GATA4, ANP, α-ca-actin, TnT, MLC2v, MLC2a, α-MHC (α-myosin heavy chain), β-MHC (β-myosin heavy chain)) in cardiac myocytes differentiated from human-derived sphere-forming cells. Note that in the present analysis, β-actin was used as control.

FIG. 16 shows photograph of smooth myocytes differentiated from human-derived sphere-forming cells.

FIG. 17 shows the result of analysis by PCR of the expression of various markers (SM-22α and calponin) in smooth myocytes differentiated from human-derived sphere-forming cells. Note that in the present analysis, β-actin was used as control.

FIG. 18 shows photograph of vascular endothelial cells differentiated from human-derived sphere-forming cells.

FIG. 19 shows the result of analysis by PCR of the expression of various markers (CD31 and VEGF-R2) in vascular endothelial cells differentiated from human-derived sphere-forming cells. Note that in the present analysis, β-actin was used as control.

FIG. 20 shows the state of grafting in a mouse cardiac muscle, wherein the human-derived sphere-forming cells (pluripotent stem cells) obtained in Example 3 were transplanted into an infarcted mouse cardiac muscle. A is a figure showing cells (presenting a red color by cTnI staining), which were human-derived sphere-forming cells differentiated into cardiac myocytes and grafted in a host cardiac muscle. B is a figure where a figure in which intracellular nuclei were stained in blue using DAPI in the same visual field as A, and A have been overlaid. C is a figure showing that cardiac myocytes (presenting a red color by cTnI staining) differentiated from human-derived sphere-forming cells, are also grafted in the central portion of the myocardial infarction. D is a figure showing cells that are human-derived sphere-forming cells differentiated into cardiac myocytes (presenting a red color by cTnI staining) and grafted inside a thinned infarct. E is a figure where a figure in which intracellular nuclei were stained in blue using DAPI in the same visual field as D, and D have been overlaid. F is a figure showing nuclei stained in blue using DAPI and CD31-positive vascular endothelial cells stained in red by the staining of CD31. F shows that human-derived CD31-positive vascular endothelial cell differentiated from sphere-forming cells are grafted.

BEST MODE FOR CARRYING OUT THE INVENTION

Hereinafter, the present invention will be described in detail.

A. Method for Preparing the Stem Cell of the Present Invention

Hereinafter, the method for preparing the pluripotent stem cells of the present invention will be described in detail step by step.

1. Preparation of Cell Suspension

First, a cell suspension is prepared by treating enzymatically a cardiac tissue fragment taken from a mammal (Step (i)).

In the present invention, the cardiac tissue serving as the source for the collection of pluripotent stem cells is not limited in particular, as long as it is mammal-derived. In the present invention, for instance, mouse, rat, guinea pig, hamster, rabbit, cat, dog, sheep, pig, cow, goat, monkey, human and the like, may be cited as mammals. When using in the treatment of a human cardiac disease the pluripotent stem cells to be prepared, it is preferable that the tissue is human-derived. In addition, the site of cardiac tissue used in the present step is also not limited in particular.

The collection of a cardiac tissue fragment from a mammal is carried out by excising a cardiac tissue fragment by a conventional surgical method. In addition, it is desirable that tissues other than cardiac tissue (for instance, blood vessel, nerve tissue and the like) are removed as much as possible in the excised cardiac tissue fragment, prior to the enzymatic treatment. In addition, in order to increase the efficiency of enzymatic treatment, it is desirable that the collected cardiac tissue fragment is chopped into fragments of approximately 1 mm$^3$ or less prior to being subjected to enzymatic treatment.

In addition, the enzymatic treatment is carried out using enzymes generally used when preparing a cell suspension from a biological tissue fragment. Specific examples of enzymes include proteases such as collagenase, trypsin, chymotrypsin, pepsin, etc. Among these, collagenase is preferable. Specific example of the collagenase includes collagenase type 2 (manufactured by Worthington; 205 U/mg). Note that in the present specification, collagenase 1

U represents the amount of enzyme that allows 1 µmol of L-leucine to be liberated from collagen at pH7.5, 37° C. and in 5 hours.

In addition, there are also no particular limitations regarding the enzymatic treatment conditions, and as one example, the following enzymatic treatment conditions are illustrative:

Enzyme Concentration:

For example, if collagenase type 2 (manufactured by Worthington; 205 U/mg) is to be used, enzyme concentration is typically from 0.1 to 0.3 wt. % and preferably about 0.2 wt. % when treating mouse-derived cardiac muscle tissue, and typically from 0.2 to 0.6 wt. % and preferably about 0.4 wt. % when treating human-derived cardiac muscle tissue. In addition, for example, enzyme concentration per 100 mg of cardiac muscle tissue is typically from 4100 to 12300 U, and preferably about 8200 U.

Treatment Temperature:

Temperature is typically about 37° C.

Treatment Duration and Times:

Conditions are exemplified by conditions where the enzymatic treatment is repeated twice with a treatment duration of typically 20 to 30 minutes, and preferable conditions where the enzymatic treatment is repeated twice with a treatment duration of about 20.

It is desirable that the cell suspension obtained in this manner, after enzymatic treatment, is treated by centrifugal separation to remove the supernatant and adding culture medium appropriate for the growth of the cells. Examples of culture medium appropriate for the growth of the cells include Dulbecco's Modified Eagle Medium (DMEM) culture medium containing 10 vol. % fetal bovine serum (FBS) and 1 vol. % penicillin-streptomycin (mixture of 5000 U/ml penicillin and 5000 µg/ml streptomycin sulfate).

2. Separation of Group of Cardiac Tissue-Derived Cells

Next, a group of cardiac tissue-derived cells is separated from the above cell suspension by the density gradient method (Step (ii)).

In the present step, the separation of the group of cardiac tissue-derived cells can be performed by the density gradient method, which is typically adopted for the separation of cells. Example of preferred mode of separation of group of cardiac tissue-derived cells include the method of separating a group of cardiac tissue-derived cells by percoll density gradient centrifugation. Percoll density gradient centrifugation is a well-known method using percoll, which is one type of silica gel, to carry out centrifugal separation, and as percoll is used in layers, separation is possible without destroying the cells due to centrifugal force.

In order to separate the group of cardiac tissue-derived cells containing the target stem cells from the above cell suspension by percoll density gradient centrifugation, for example, a centrifugal fractionation in a discontinuous density gradient comprising 30 vol. % percoll solution and 70 vol. % percoll solution at room temperature and 1000 G, for 20 minutes, of the above-mentioned cell suspension, is adequate, whereby a group of cardiac tissue-derived cells containing the target stem cells is obtained at the interface of the 30 vol. % percoll solution and the 70 vol. % percoll solution.

3. Separation of Pluripotent Stem Cells

Next, after suspension-culturing the group of cardiac tissue-derived cells obtained in the above Step (ii) in a culture medium containing epidermal growth factor (EGF) and fibroblast growth factor (FGF), cells forming a floating sphere (cell mass) are selected and separated (Step (iii)).

Prior to the suspension culture, it is desirable to subject the group of cardiac tissue-derived cells obtained in the above Step (ii) to a further enzymatic treatment to eliminate cell-to-cell bonds and attachment. Such enzymatic treatment has no particular limitation on the specific methods therefor, and can be carried out via well-known methods using a protease or the like. Examples of the enzymatic treatment include the method whereby the group of cardiac tissue-derived cells are treated in a solution containing 0.05 wt. % trypsin and 0.53 mM EDTA, at 37° C. for about 10 minutes. In addition, following the enzymatic treatment, it is desirable that a protease inhibitor is added to inactivate the protease activity before subjection to the present Step (iii).

A culture medium used in a conventional cell culture (suspension culture) to which epidermal growth factor and fibroblast growth factor have been added is sufficient for the culture medium used in the present step. Examples of preferred culture medium include a culture medium comprising a DMEM/F12HAM medium containing human serum or bovine serum albumin to which the above epidermal growth factor and fibroblast growth factor have been added. In addition, the culture medium used in the present step may contain, if necessary, antibiotics such as streptomycin, kanamycin and penicillin, B27 supplement (manufactured by GIBCO), HEPES (5 mM), and the like.

For example, the proportion of epidermal growth factor and fibroblast growth factor added to culture medium in the present step is 10 to 20 ng/ml, and preferably about 20 ng/ml of epidermal growth factor; and 10 to 40 ng/ml, and preferably about 40 ng/ml of fibroblast growth factor.

In the present step, it is desirable that the cell concentration at culture start time is set to $1 \times 10^4$ to $2 \times 10^4$ cells/ml, and preferably $2 \times 10^4$ cells/ml, to carry out the culture.

The suspension culture in the present step is carried out typically at 37° C., under 5% $CO_2$, typically for 14 to 21 days, preferably for 14 days.

By carrying out a culture in this way, pluripotent stem cells repeat cell divisions to form a sphere (cell mass), which floats in the culture solution. Consequently, by recovering this sphere, the target pluripotent stem cells can be obtained.

B. Characteristics of Pluripotent Stem Cells

The mammalian cardiac tissue-derived pluripotent stem cells obtained in this way have the capability to differentiate into various mature cells such as cardiac myocyte as well as self-renewal capability. Examples of cells that the pluripotent stem cells can differentiate into include cardiac myocyte, smooth myocyte, vascular endothelial cell, adipocyte, glial cell and epithelial cell. In particular, the pluripotent stem cells have excellent differentiation capability into cardiac myocytes, which can be cited as one characteristic.

Properties of the cell surface antigens of the pluripotent stem cells obtained by the above preparation method are exemplified by c-kit-negative, CD31-negative and CD34-negative. Furthermore, the pluripotent stem cells are exemplified by those showing CD105-positive as a property of the cell surface antigens. In addition, the pluripotent stem cells are exemplified by those showing Sca-1-positive, CD45-negative, CD38-positive and CD90-positive as property of the cell surface antigens. Such properties of cell surface antigens can be determined by a well-known methods. In addition to the method of carrying out the above suspension culture (above Step (iii)), pluripotent stem cells having such properties of cell surface antigens can also be obtained through fractionation of cells having the above-mentioned cell surface antigen characteristics from the group of cardiac tissue-derived cells obtained in the above Step (ii) by well-known methods. Examples of method for fractionating cells in this way include methods using a flow cytometer provided with a sorting function.

C. Culture (Proliferation) of Pluripotent Stem Cells

Culturing the above pluripotent stem cells in a culture medium containing epidermal growth factor and fibroblast growth factor allow the pluripotent stem cells to be proliferated (Step (iv)).

In the present step, it is desirable to break down the sphere prior to the culture by treating the sphere obtained in the above Step (iii) with a protease, and suspend the pluripotent stem cells. The method for suspending pluripotent stem cells in this way can be exemplified by the method of treating with trypsin at a concentration of 0.05 wt. %, for about 20 minutes at 37° C. After the protease treatment, it is desirable to add a protease inhibitor to inhibit the action of the protease.

In addition, the culture mediums used in the present step is the same as those used in the previous Step (iii).

In the present step, the above pluripotent stem cells can be proliferated to the desired quantity, for example, by carrying out culture with a cell concentration at culture start time of 20 cells/μl, at 37° C., under 5% $CO_2$, and typically for 14 to 21 days.

D. Induction of Differentiation of the Pluripotent Stem Cells into Target Cells

Method for inducing differentiation of the above pluripotent stem cells into various cells such as cardiac myocyte can be exemplified by the method of culturing the proliferated above pluripotent stem cells in a medium containing dexamethasone.

In regard to the proportion of added dexamethasone in the culture medium used for the induction of differentiation, there is no particular limitation as long as induction of differentiation into cardiac myocyte is possible, and typically, it is adequate that dexamethasone is contained at a proportion of about $1 \times 10^{-8}$ mol/l in the culture medium.

There is no particular limitation in regard to the type of culture medium used in the induction of differentiation. Preferred culture medium can be exemplified by an MEM culture medium (minimum essential medium, manufactured by GIBCO) into which dexamethasone was added. In addition, similarly to culture media used for the proliferation of pluripotent stem cells, the culture medium may contain, if necessary, antibiotics such as streptomycin, kanamycin and penicillin, HEPES (5 mM) and the like.

Culturing the above pluripotent stem cells using the above culture medium, typically at 37° C., under 5% $CO_2$, typically for 7 to 21 days, and preferably for on the order of 14 days, allows the above pluripotent stem cells to be induced to differentiate into various cells such as cardiac myocytes at a given proportion.

In particular, the above-mentioned method of culturing in a culture medium containing dexamethasone is preferably adopted to induce the above pluripotent stem cells to differentiate into cardiac myocytes.

Furthermore, in addition to the method for inducing differentiation using the above culture medium, the method of culturing the grown above pluripotent stem cells in a culture medium containing platelet-derived growth factor (PDGF-BB) may be cited as a method for inducing differentiation into smooth myocyte. In the method, the platelet-derived growth factor concentration in the culture medium is typically on the order of 10 ng/ml, and the culture conditions are similar to the above-mentioned case of induction of differentiation into cardiac myocyte.

Furthermore, in addition to the method for inducing differentiation using the above-mentioned culture medium, the method of culturing the proliferated above pluripotent stem cells in a culture medium containing vascular endothelial growth factor (VEGF) is exemplified as a method for inducing differentiation into vascular endothelial cell. In the method, the vascular endothelial growth factor concentration in the culture medium is typically about 10 ng/ml, and the culture conditions are similar to the above-mentioned case of induction of differentiation into cardiac myocyte.

E. Therapeutic Methods for Diseases

The above pluripotent stem cells can be used in the regeneration or repair of various tissues or organs. Specifically, in a patient having a diseased tissue or organ, transplanting a therapeutic effective amount of the above pluripotent stem cells to the diseased site of the tissue or organ allows the disease to be treated.

Preferably, diseases to be targeted in the treatment using the above pluripotent stem cells can be exemplified by cardiac diseases. As the above pluripotent stem cells are cardiac tissue-derived, the capability of differentiation into cardiac myocyte is particularly excellent, such that it is used preferably for treatments against cardiac diseases, among the above-mentioned diseases.

Targeted cardiac diseases can be exemplified by cardiac diseases such as those damaging a cardiac muscle or the coronary artery and decreasing contractile force, and specifically can be exemplified by myocardial infarction, dilated cardiomyopathy, ischemic cardiac disease, congestive heart failure, and the like.

Methods for transplanting a pluripotent stem cell can be exemplified by the method of using a catheter to inject the above pluripotent stem cells to the diseased site of the tissue or the organ targeted for treatment, or the method of practicing an incision to inject the above pluripotent stem cells directly to the diseased site of the tissue or the organ targeted for treatment, and the like.

In addition, regarding the administration amount of the pluripotent stem cells to be transplanted to the affected area, it is suitably set according to the type of the disease, the extent of the symptoms, the age and the sex of the patient, and the like, and for example, $1.0 \times 10^6$ to $1.0 \times 10^8$ pluripotent stem cells can be administered in one transplantation.

In the therapeutic method of the present invention, although a pluripotent stem cells collected from another person than the patient having the disease may be used, the use of the patient's own cardiac tissue-derived pluripotent stem cells are desirable from the point of view of suppressing rejection.

Note that, therapeutic method of the present invention includes as therapeutic method for cardiac diseases, method with the following modes:

Therapeutic method for a cardiac disease comprising the following Steps (i) to (v):

(i) a step of enzymatically treating a cardiac tissue fragment collected from a human to prepare a cell suspension, (ii) a step of separating a group of cardiac tissue-derived cells from the above cell suspension by the density gradient method, and (iii) a step of suspension-culturing the obtained group of cardiac tissue-derived cells in a culture medium containing fibroblast growth factor and epidermal growth factor, and then selecting and separating cells forming a floating sphere, (iv) a step of proliferating the cells separated in the above Step (iii), and (v) a step of transplanting the cells proliferated in the above Step (iv) into the heart of a cardiac disease patient.

F. Composition for the Treatment of a Tissue or Organ Disease

As described above, the above pluripotent stem cells are useful for the treatment of a tissue or organ disease. Therefore, the present invention further provides a composition for the treatment of tissue or organ disease containing the above pluripotent stem cells and a pharmaceutically acceptable carrier. The composition is used by being administered to the diseased site, in the treatment of a tissue or organ disease.

Herein, for example, physiological saline, buffer solution, or the like, is used as a pharmaceutically acceptable carrier. In addition, regarding the amount of above pluripotent stem cells mixed in the composition for the treatment, it is suitably set based on the amount of pluripotent stem cells to be transplanted to the affected area.

In particular, the composition is excellent as a composition for the treatment of cardiac disease, because the above pluripotent stem cells are cardiac tissue-derived and their capability of differentiation into cardiac myocyte is excellent.

EXAMPLES

Hereinafter, the present invention will be described in detail based on examples; however, the present invention is not limited to these.

Example 1

Obtainment of Mouse-Derived Pluripotent Stem Cells and Induction of Differentiation of the Stem Cells
(1) Preparation of Cell Suspension A 6 to 8 weeks-old female C57Bl/6J mouse (manufactured by Shimizu Laboratory Supplies Co., Ltd) (hereinafter, may be noted wild-type mouse) or a mouse obtained by conferring green fluorescent protein (GFP) expression capability to the same mouse (hereinafter, may be noted GFP-expressing mouse) was euthanized under diethyl ether anesthesia by manual cervical dislocation, and immersed in an aqueous solution of 70 vol. % ethyl alcohol to disinfect the entire body. Using pointed tweezers and scissors that have undergone high pressure steam sterilization beforehand, median sternotomy was performed and the heart was extracted. The extracted heart was placed inside a petri dish containing cold PBS (Phosphate buffered saline) on ice, and using a syringe fitted with a 23 gauge needle, 2 ml of cold PBS was injected three times from the aortic valve ring to eliminate intracardiac blood. Next, an incision was practiced in the midsection of the heart, and the heart cavities were washed in a new petri dish containing cold PBS. Furthermore, this washing of heart cavities was repeated twice, and PBS was eliminated at the end. Thereafter, cardiac tissue fragments that were fragmented using sterilized scissors were shredded so they were approximately 1 mm$^3$ or less. The shredded cardiac tissue fragments (approximately 100 mg) were transferred to a 100 ml-capacity Erlenmeyer flask, 20 ml of a solution containing 0.2 wt. % collagenase type2 (manufactured by Worthington) was further added, and enzymatic treatment was carried out by shaking for 20 minutes inside a 37° C. constant temperature chamber. Next, further using a 10 ml electric pipetor, pipetting was performed at a speed of 3 ml/sec and the content was stirred well, then 2.2 ml of a solution containing 0.1 wt. % DNAse I (manufactured by Worthington) was further added, and [the solution] was shaken for 3 minutes inside a 37° C. constant temperature chamber. After the enzymatic treatment, the enzyme was neutralized by the addition of 20 ml of DMEM (manufactured by GIBCO) culture medium containing 10 vol. % FBS (fetal bovine serum) (manufactured by Hyclone) and 1 vol. % penicillin-streptomycin (hereinafter, noted "Culture Medium 1") to prepare a cell-containing solution, then, the solution was filtered with a 70 μm cell strainer (manufactured by FALCON) and a 40 μm cell strainer (manufactured by FALCON). The cell-containing solution after filtration was subjected to centrifugal separation for 5 minutes at 1500 rpm, the supernatant thereof was eliminated, then, 10 ml of Culture Medium 1 was added to prepare a cell suspension (hereinafter, noted Cell Suspension 1), and this was conserved in ice. In addition, the same treatment was performed again on the cardiac tissue fragments remaining in the 100 ml-capacity Erlenmeyer flask, and a cell suspension was prepared similarly (hereinafter, noted Cell Suspension 2). The Cell Suspensions 1 and 2 obtained in this way were mixed and subjected to the steps described below.

(2) Separation of a Group of Cardiac Tissue-Derived Cells by Percoll Density Gradient Centrifugation A solution of percoll stock solution (manufactured by Amersham Biosciences): 10×PBS (−) (manufactured by GIBCO)=9:1 (volume ratio) served as the percoll stock. The percoll stock was diluted with 1×PBS (−) (manufactured by GIBCO) to prepare solutions with percoll stock concentrations of 30 vol. % and 70 vol. %. The 30 vol. % percoll solution was colored by the addition of 0.1 vol. % phenol red (manufactured by SIGMA). In a conical tube with a capacity of 15 ml, 3 ml of 30 vol. % percoll solution was first poured, then, using an electric pipetor, 70 vol. % percoll solution was carefully added below the 30 vol. % percoll solution. Next, 3 ml of the above-mentioned cell suspension derived from wild-type mouse or GFP-expressing mouse was carefully overlaid above the 30 vol. % percoll solution. Centrifugal fractionation was performed at room temperature, 1000 G and for 20 minutes, with as slow as possible acceleration and deceleration. After centrifugation, a group of the target cells was observed to be distributed at the interface of the 30 vol. % percoll solution and 70 vol. % percoll solution. In addition, it was observed that blood cell components were distributed at the bottom, and cell debris was distributed mainly in the upper layer of 30 vol. % percoll. First, cell debris were eliminated by using a Pasteur pipette, then, with another pipette, the group of the target cells present at the interface was recovered in a conical tube with a capacity of 50 ml. After 30 ml of DMEM/F12Ham (manufactured by GIBCO) culture medium was added to the conical tube and the content was stirred sufficiently, centrifugation was carried out and the supernatant was eliminated. Then, 1 ml of trypsin-EDTA (containing 0.05 wt. % trypsin and 0.53 mM EDTA.4Na) (manufactured by GIBCO) solution was added, and the content was shaken inside a 37° C. constant temperature chamber for 10 minutes to eliminate cell-to-cell agglutination and bonding. Then, 500 μl of trypsin inhibitor (manufactured by Roche) was added, 8.5 ml of DMEM/F12Ham culture medium (manufactured by GIBCO) was further added, suspending sufficiently, then the cell number was counted with a blood cell counting plate.

(3) Sphere Formation-1

Suspension culture of the group of cardiac tissue-derived cells derived from wild-type mouse or GFP-expressing mouse obtained in (2) above was carried out using mouse expansion medium [containing DMEM/F12Ham (manufactured by GIBCO), 2 wt. % B27 supplement (manufactured by GIBCO), 1 vol. % penicillin-streptomycin, 40 ng/ml recombinant human basic FGF (manufactured by Promega), and 20 ng/ml mouse EGF (manufactured by SIGMA)], on a cell culture dish (noncoat cell culture dish) (manufactured by Becton Dickinson), at 37° C., under 5% $CO_2$ and for 14 days. Note that the cell concentration at culture start time was set to be $2.0\times10^4$ cells/ml.

After culturing in this way, a sphere (cell mass) floating in the culture solution was retrieved.

(4) Sphere Formation-2

As references, the group of wild-type mouse cardiac tissue-derived cells obtained in (2) above and the group of GFP-expressing mouse cardiac tissue-derived cells obtained in (2) above were mixed at a proportion of 1:1, and a suspension culture was carried out with similar conditions as in (3) above.

Results of observation of sphere floating in the culture solution after the culture are shown in FIG. 1. In FIG. 1, A, C, E and G show photographs taken under a fluorescence microscope, B, D, F and H show photographs under from a phase contrast microscope. Note that with the fluorescence microscope, only GFP-expressing mouse-derived spheres are observed, and with the phase contrast microscope, spheres from both the wild-type mouse and the GFP-expressing mouse are observed. A and B, C and D, E and F, and G and H are the same visual fields photographed respectively. From the photographs A and B, wild-type mouse-derived spheres and GFP-expressing mouse-derived spheres were shown to co-exist in the culture solution. In addition, a sphere having an identical shape in both photographs C and D was observed, showing that the sphere that is the subject in C and D was GFP-expressing mouse-derived. On the other hand, from the facts that no sphere was pictured in photograph E and that a sphere was observed in photograph F, it is clear that the sphere that is the subject in E and F was wild-type mouse-derived. In addition, from the fact that spheres of different shapes were observed in the photographs G and H, it is clear that the sphere that is the subject in G and H was formed from mixed wild-type mouse-derived cells and GFP-expressing mouse-derived cells.

(5) Proliferation of Sphere-Forming Cells

The recovered sphere was placed into a 2 ml of DMEM/F12Ham (manufactured by GIBCO) culture medium, which was mixed well, then, this was subjected to centrifugal separation (4° C., 1500 rpm, 5 minutes), and supernatant was eliminated sufficiently. Then, 1 ml of a solution of trypsin-EDTA (containing 0.05 wt. % trypsin and 0.53 mM EDTA.4Na) (manufactured by GIBCO) was added, and sphere was broken down by shaking for 20 minutes inside a 37° C. constant temperature chamber to float cells forming the sphere (hereinafter, noted sphere-forming cells). Next, 500 µl of trypsin inhibitor (manufactured by Roche) was added to suspend sufficiently, and then the cell number was counted with a blood cell counting plate.

Thus-floated sphere-forming cells were cultured with mouse expansion medium [containing DMEM/F12Ham (manufactured by GIBCO), 2 wt. % B27 supplement (manufactured by GIBCO), 1 vol. % penicillin-streptomycin, 40 ng/ml recombinant human basic FGF (manufactured by Promega), and 20 ng/ml mouse EGF (manufactured by SIGMA)], at a cell concentration of culture starting time of 20 cells/µl, on a fibronectin coating cell culture dish, at 37° C., under 5% $CO_2$ and for 3 days.

(6) Determination of the Characteristics of Sphere-Forming Cells

FACS analysis was performed on the sphere-forming cells proliferated in (5) above for various cell surface antigens (Sca-1, c-kit, CD34, CD45, CD31, CD38, CD90 and CD105). The result obtained is shown in FIG. 2. From this result, the obtained sphere-forming cells were determined to be c-kit-negative, CD31-negative and CD34-negative, and be further CD105-positive. In addition, the cells were also determined to be Sca-1-positive, CD45-negative, CD38-positive and CD90-positive.

Furthermore, the sphere-forming cells proliferated in (5) above were also analyzed by PCR for the expression of various markers (Bmi 1, TERT, Bcrp 1, Oct 4, UTF 1, Nanog, Brachyury, Sox 2, Nestin, and Islet 1). The result obtained is shown in FIG. 3. As a result of this, it was determined that no expression of Oct 4 and UTF 1, which are markers of embryonic stem cell, was observed in the sphere-forming cells. On the other hand, it was determined that expressions of Brachyury, which is a marker of mesoblastic stem cells, and Sox 2 and Nestin, which are markers of ectodermal stem cells, were observed in the cells. In addition, from the fact that they strongly express Bmi 1 and TERT, the cells are suggested to have high self-renewal capability.

In addition, the sphere obtained in (3) above was attached to a slide via cytospin, and bromodeoxyuridine (BrdU) staining was carried out, to determine the presence or the absence of BrdU inside the sphere-forming cells. This result is shown in FIG. 4. As is clear from FIG. 4, it was determined that approximately half the number of sphere-forming cells are BrdU-positive, and that cell division is occurring actively.

And furthermore, the expression of telomerase was analyzed in the sphere obtained in (3) above. Note that for the analysis, 5, 10 or 30 spheres served as samples, using these with heat treatment (85° C., 15 minutes) (heat (+)) and without heat treatment (heat (−)), and further, telomer-positive cells (positive control), culture medium only (negative control) and telomer template (positive template) were also analyzed as control samples. The result obtained is shown in FIG. 5. As a result of this, it was determined that telomerase was strongly expressed in the sphere obtained in (3) above.

(7) Determination of Differentiation into Cardiac Myocyte

The sphere-forming cells proliferated in (5) above were recovered by centrifugal separation, and the cells were cultured in a MEM culture medium (manufactured by GIBCO) containing $1\times10^{-8}$ mol/l dexamethasone and 1 vol. % penicillin-streptomycin, at 37° C., under 5% $CO_2$ and for 21 days. It was determined that the above-mentioned sphere-forming cells differentiate into beating cardiac myocytes by this culture. In addition, photographs used to observe the morphology of the cell in the culture is shown in FIG. 6. As shown in FIG. 6, the sphere-forming cells were found to proliferate and differentiate in a concentric circular shape, in the differentiation process into cardiac myocyte. Note that differentiation into cardiac myocyte was also determined from the following analytical results.

<Analysis by Cardiac Muscle-Specific Troponin-I Staining>

When cells after 21 days culture were stained with cardiac muscle-specific troponin-I and observed, the presence of cardiac myocyte was determined (refer to FIG. 7).

<Analysis by PCR>

The expression of various markers (Nkx 2.5, GATA 4, ANP, troponin-I (TnI), MLC2v, MLC2a, α-MHC (α-myosin heavy chain) and β-MHC (β-myosin heavy chain)) in cultured cells was analyzed by PCR, 21 days after the start of induction of differentiation. The result obtained is shown in FIG. 8. As a result of this, it was determined that the expression of cTnI and α-MHC, which are marker for cardiac myocyte, was strongly observed.

(8) Determination of Differentiation into Other Cells

In order to determine the capability of differentiation into smooth myocyte, vascular endothelial cell, adipocyte, glial cell and epithelial cell, inductions of differentiation were carried out on the sphere-forming cells proliferated in (5) above (refer to A in FIG. 9), with the following methods.

(8-1) Differentiation into Smooth Myocyte

The sphere-forming cells proliferated in (5) above were recovered by centrifugal separation, and the cells were cultured in a MEM culture medium (manufactured by GIBCO) containing $1\times10^{-8}$M dexamethasone, at 37° C., under 5% $CO_2$ and for 14 days. When the cells after the culture were stained using α-SMA (α-smooth muscle actin) and observed, the presence of smooth myocyte was determined (refer to B in FIG. 9).

(8-2) Differentiation into Endothelial Cell

The sphere-forming cells proliferated in (5) above were recovered by centrifugal separation, and the cells were cultured in a MEM culture medium (manufactured by GIBCO) containing $1\times10^{-8}$M dexamethasone, at 37° C., under 5% $CO_2$ and for 14 days. When the cells after the culture were stained using CD31 and observed, the presence of CD31-positive vascular endothelial cells was determined (refer to C in FIG. 9).

(8-3) Differentiation into Adipocyte

The sphere-forming cells proliferated in (5) above were recovered by centrifugal separation, and the cells were cultured in a MEM culture medium (manufactured by GIBCO) containing $1\times10^{-8}$M dexamethasone, at 37° C., under 5% $CO_2$ and for 14 days. When oil-red staining was performed on the cells after the culture, the presence of oil-red-positive adipocytes was determined (refer to D in FIG. 9).

(8-4) Differentiation into Glial Cell

The sphere-forming cells proliferated in (5) above were recovered by centrifugal separation, and the cells were cultured in a MEM culture medium (manufactured by GIBCO) containing $1\times10^{-8}$M dexamethasone, at 37° C., under 5% $CO_2$ and for 14 days. When the morphological characteristics of the cells after the culture were observed, the presence of glial cells was determined (refer to E in FIG. 9).

(8-5) Differentiation into Epithelial Cell

The sphere-forming cells proliferated in (5) above were recovered by centrifugal separation, and the cells were cultured in a MEM culture medium (manufactured by GIBCO) containing $1\times10^{-8}$M dexamethasone, at 37° C., under 5% $CO_2$ and for 14 days. When the morphological characteristics of the cells after the culture were observed, the presence of epithelial cells was determined (refer to F in FIG. 9).

(9) Result

From the results of Example 1 shown above, the obtained sphere-forming cells were found to have self-renewal capability together with the property of differentiating into various cells, and to be pluripotent stem cells.

Example 2

Transplantation of Mouse-Derived Myocardial Stem Cells

The GFP-expressing mouse-derived sphere-forming cells (pluripotent stem cells) obtained in the above Example 1 were cultured and proliferated in mouse expansion medium [containing DMEM/F12Ham (manufactured by GIBCO), 2 wt. % B27 supplement (manufactured by GIBCO), 1 vol. % penicillin-streptomycin, 40 ng/ml recombinant human basic FGF (manufactured by Promega) and 20 ng/ml mouse EGF (manufactured by SIGMA)]. Thereafter, the proliferated stem cells (approximately $1\times10^6$ cells) were suspended in 15 µl of PBS (−) (manufactured by GIBCO), this was transplanted using BD Ultra Fine II lancet (manufactured by Becton Dickinson) into an infarcted cardiac muscle created in a 10 to 12 weeks-old NOD/SCID mouse (purchased from Jackson Laboratory). The heart was extracted from the mouse 21 days after transplantation of the stem cells. The cardiac muscle of the extracted heart was checked for the grafting to the host cardiac muscle of the stem cells showing green fluorescence (GFP) (refer to the A in FIG. 10). In addition, cTnT staining (identified in red) was performed in an identical visual field to the A in FIG. 10 (refer to the B in FIG. 10). When the A and the B in FIG. 10 are overlaid, the presence of stem cells (green) and the presence of cTnI expression (red) are overlapped (refer to the C and the D in FIG. 10). From the facts, it is determined that the transplanted cardiac tissue-derived stem cells differentiated into cardiac myocytes, contributing to repairing the heart.

Example 3

Obtainment of Human-Derived Pluripotent Stem Cell and Induction of Differentiation of the Stem Cell into Various Cells Using cardiac tissue fragments collected from human, a group of human cardiac tissue-derived cells was separated according to the methods described in "(1) Preparation of cell suspension" and "(2) Separation of a group of cardiac tissue-derived cells by percoll density gradient centrifugation" of the above Example 1.

Next, using the obtained cell group, a culture was carried out according to the methods described in "(3) Sphere formation-1" of the above Example 1, to form a sphere. Photomicrographs of a sphere floating in the culture solution taken one day after and seven days after the culture are shown in FIG. 11. After the culture, human cardiac tissue-derived sphere-forming cells (pluripotent stem cells) were obtained by recovering the sphere.

The recovered sphere-forming cells were proliferated by carrying out a culture according to the methods of "(5) Proliferation of sphere-forming cell" described in the above Example 1. The sphere-forming cells after culture were analyzed by PCR for the expression of various markers (Rex 1, TERT, Oct 4, Nanog, Brachyury and Sox 2). The result is shown in FIG. 12. From this result, human cardiac tissue-derived sphere-forming cells were determined to have similar differentiation properties to ectodermal stem cells and embryonic stem cells.

In addition, the proliferated sphere-forming cells were analyzed for various cell surface antigens (c-kit, CD34, CD90 and CD105). The analytical result is shown in FIG. 13. From this result, the human-derived sphere-forming cells were determined to be c-kit-negative, CD34-negative, CD90-positive and CD105-positive.

Differentiation into Cardiac Myocyte

The proliferated sphere-forming cells were induced to differentiate into cardiac myocyte was performed according to the methods of "(7) Determination of differentiation into cardiac myocyte" described in the above Example 1. This determined that the human cardiac tissue-derived sphere-forming cells differentiate into beating cardiac myocytes. Note that differentiation into cardiac myocyte was also determined from the following analytical results.

<Analysis by Human Cardiac Muscle-Specific Troponin-T Staining>

When cells after induction of differentiation were stained with human cardiac muscle-specific troponin-T and observed, the presence of cardiac myocyte was identified (Refer to FIG. 14).

<Analysis by PCR>

Cells at 21 days after the start of induction of differentiation were analyzed by PCR for the expression of various markers (Nkx-2.5, GATA4, ANP, α-ca-actin, TnT, MLC2v, MLC2a, α-MHC (α-myosin heavy chain), β-MHC (β-myosin heavy chain) and β actin). The obtained result is shown in FIG. 15. As is clear from FIG. 15, it was determined that the above various markers were expressed and the above human cardiac tissue-derived sphere-forming cells differentiated into cardiac myocytes by culturing in the presence of dexamethasone.

Differentiation into Smooth Myocyte

The proliferated sphere-forming cells were induced to differentiate according to the methods of "(8-2) Differentiation into vascular endothelial cell" described in the above-mentioned Example 1. This determined that the human cardiac tissue-derived sphere-forming cells differentiate into smooth myocytes. Note that the differentiation into cardiac myocyte was also determined from the following analytical results.

<Analysis by Microscopy>

When α-SMA was stained in the cells after induction of differentiation and observed, the presence of smooth myocyte was determined (refer to FIG. 16).

<Analysis by PCR>

Cells at 21 days after the start of induction of differentiation were analyzed by PCR for the expression of various markers (SM-22α and calponin). The obtained result is shown in FIG. 17. As is clear from FIG. 17, it was determined that, the above markers were expressed and the above human cardiac tissue-derived sphere-forming cells differentiated into smooth myocytes, after the induction of differentiation.

Differentiation into Vascular Endothelial Cell

The proliferated sphere-forming cells were induced to differentiate into endothelial cell according to the methods of "(4) Determination of differentiation into other cells" described in the above Example 1. This determined that the human cardiac tissue-derived sphere-forming cells differentiated into vascular endothelial cells. Note that the differentiation into vascular endothelial cell was also determined from the following analytical results.

<Analysis by Microscopy>

When CD31 was stained in the cells after induction of differentiation and observed, the presence of endothelial cell was determined (Refer to FIG. 18).

<Analysis by PCR>

Cell after induction of differentiation were analyzed by PCR for the expression of various markers (CD31 and VEGF-R2). The obtained result is shown in FIG. 19. As is clear from FIG. 19, the above markers were expressed and the above human cardiac tissue-derived sphere-forming cells differentiated into vascular endothelial cells, after induction of differentiation.

Result

From the results of Example 3 shown above, the obtained human-derived sphere-forming cells were found to have self-renewal capability and at the same time the property of differentiating into various cells, and to be pluripotent stem cells.

Example 4

Transplantation of Human-Derived Myocardial Stem Cells

The human cardiac tissue-derived sphere-forming cells (pluripotent stem cells) obtained in the above Example 3, were cultured and proliferated in human expansion medium [containing DMEM/F12Ham (manufactured by GIBCO), 1 vol. % penicillin-streptomycin, 40 ng/ml recombinant human basic FGF (manufactured by Promega), and 20 ng/ml human EGF (manufactured by SIGMA)]. Thereafter, the proliferated human cardiac tissue-derived pluripotent stem cells (approximately $1\times10^6$ cells) were transplanted into an ischemic cardiac muscle mouse by the same method of above Example 2. The heart was extracted from the mouse 21 days after transplantation of myocardial stem cells. Nuclei in the cells of the cardiac muscle of the extracted heart were stained in blue using DAPI (4'6-diamino-2-phenylindole). Furthermore, cardiac myocytes differentiated from sphere-forming cells were stained in red using human cardiac muscle-specific troponin-T. As a result of this, it was determined that the human cardiac tissue-derived cells transplanted into the thinned infarct migrated and grafted, and mainly the endocardium side was regenerated by new cardiac myocytes (refer to A to E in FIG. 20). In addition, when CD31 staining was performed concomitantly on the extracted heart, it was determined that human cardiac tissue-derived cells also differentiated into vascular endothelial cells and grafted (refer to F in FIG. 20).

The invention claimed is:

1. A method for treating a cardiac tissue or organ in need of repair and/or regeneration in a patient comprising:
   transplanting a therapeutically effective amount of an enriched cell population of isolated human cardiac tissue-derived pluripotent stem cells into the cardiac tissue or organ in need of repair and/or regeneration in the patient,
   wherein the pluripotent stem cells are at least c-kit-negative, CD34-negative, CD105-positive, and CD90-positive, and have the capability of differentiating into one or more species of cells selected from the group consisting of cardiac myocyte, smooth myocyte, and vascular endothelial cell.

2. The method according to claim 1, wherein the pluripotent stem cells are additionally CD31-negative.

3. The method according to claim 1, wherein the pluripotent stem cells have the capability to differentiate at least into a cardiac myocyte.

4. The method according to claim 1, wherein the pluripotent stem cells are prepared from cardiac tissue fragments of the patient.

5. The method according to claim 1, wherein the pluripotent stem cells are obtained by a method comprising:
   (i) enzymatically treating a cardiac tissue fragment collected from a human to prepare a cell suspension;
   (ii) fractionating cell debris in an upper layer and blood cell components at the bottom by a density gradient method to separate a cardiac tissue-derived cell population existing at an interface from said cell suspension; and
   (iii) suspension-culturing the obtained cardiac tissue-derived cell population in a culture medium containing fibroblast growth factor and epidermal growth factor, and then selecting and separating cells forming a floating sphere.

6. A method for treating a cardiac tissue or organ in need of repair and/or regeneration in a patient, comprising:

transplanting a therapeutically effective amount of a composition comprising an enriched cell population of isolated human cardiac tissue-derived pluripotent stem cells and a pharmaceutically acceptable carrier into the cardiac tissue or organ in need of repair and/or regeneration in the patient, wherein the pluripotent stem cells are at least c-kit-negative, CD34-negative, CD105-positive, and CD90-positive, and have the capability of differentiating into one or more species of cells selected from the group consisting of cardiac myocyte, smooth myocyte, and vascular endothelial cell.

7. The method according to claim 6, wherein the pluripotent stem cells are additionally CD31-negative.

8. The method according to claim 6, wherein the pluripotent stem cells have the capability to differentiate at least into a cardiac myocyte.

9. The method according to claim 6, wherein the pluripotent stem cells are prepared from cardiac tissue fragments of the patient.

10. The method according to claim 6, wherein the pluripotent stem cells are obtained by a method comprising:
   (i) enzymatically treating a cardiac tissue fragment collected from a human to prepare a cell suspension;
   (ii) fractionating cell debris in an upper layer and blood cell components at the bottom by a density gradient method to separate a cardiac tissue-derived cell population existing at an interface from said cell suspension; and
   (iii) suspension-culturing the obtained cardiac tissue-derived cell population in a culture medium containing fibroblast growth factor and epidermal growth factor, and then selecting and separating cells forming a floating sphere.

11. The method of claim 1, wherein the cardiac tissue or organ in need of repair and/or regeneration comprises one or more of damaged cardiac muscle, damaged coronary artery, or cardiac tissue or organ with decreased contractile force.

12. The method of claim 1, wherein the cardiac tissue or organ is in need of repair and/or regeneration due to one or more of myocardial infarction, dilated cardiomyopathy, ischemic cardiac disease, or congestive heart failure.

13. The method of claim 6, wherein the cardiac tissue or organ in need of repair and/or regeneration comprises one or more of damaged cardiac muscle, damaged coronary artery, or cardiac tissue or organ with decreased contractile force.

14. The method of claim 6, wherein the cardiac tissue or organ is in need of repair and/or regeneration due to one or more of myocardial infarction, dilated cardiomyopathy, ischemic cardiac disease, or congestive heart failure.

15. A method for treating a cardiac tissue or organ that is damaged, dysfunctional, and/or hypofunctional in a patient comprising:

transplanting a therapeutically effective amount of an enriched cell population of isolated human cardiac tissue-derived pluripotent stem cells into the cardiac tissue or organ that is damaged, dysfunctional, and/or hypofunctional in the patient, wherein the pluripotent stem cells are at least c-kit-negative, CD34-negative, CD105-positive, and CD90-positive, and have the capability of differentiating into one or more species of cells selected from the group consisting of cardiac myocyte, smooth myocyte, and vascular endothelial cell.

16. The method of claim 15, wherein the cardiac tissue or organ is damaged.

17. The method of claim 15, wherein the cardiac tissue or organ is dysfunctional.

18. The method of claim 15, wherein the cardiac tissue or organ is hypofunctional.

* * * * *